US012725038B2

(12) United States Patent
Taniai et al.

(10) Patent No.: US 12,725,038 B2
(45) Date of Patent: Sep. 1, 2026

(54) PREDICTION SYSTEM, PREDICTION METHOD, AND STORAGE MEDIUM

(71) Applicant: TOYOTA JIDOSHA KABUSHIKI KAISHA, Toyota (JP)

(72) Inventors: Osamu Taniai, Okazaki (JP); Takeshi Matsui, Nissin (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 746 days.

(21) Appl. No.: 18/136,010

(22) Filed: Apr. 18, 2023

(65) Prior Publication Data

US 2024/0013045 A1 Jan. 11, 2024

(30) Foreign Application Priority Data

Jul. 5, 2022 (JP) ................................ 2022-108331

(51) Int. Cl.
*G16H 40/20* (2018.01)
*G06N 3/08* (2023.01)
*G06Q 10/02* (2012.01)

(52) U.S. Cl.
CPC ............... *G06N 3/08* (2013.01); *G06Q 10/02* (2013.01); *G16H 40/20* (2018.01)

(58) Field of Classification Search
None
See application file for complete search history.

(56) References Cited

U.S. PATENT DOCUMENTS

2007/0198357 A1* 8/2007 Ravazzolo ............. G16H 50/50 705/3
2008/0027751 A1* 1/2008 Pappalardo ............ G16H 20/13 600/300

(Continued)

FOREIGN PATENT DOCUMENTS

JP 2021-140273 A 9/2021
WO WO-2023170974 A1 * 9/2023 ............. G16H 40/20

OTHER PUBLICATIONS

Ozkil et al., Design of a robotic automation system for transportation of goods in hospitals, Proceedings of the 2007 IEEE International Symposium on Computational Intelligence in Robotics and Automation, Jun. 2007, pp. 392-397/ (Year: 2007).*

*Primary Examiner* — Anne-Marie K Alderson
(74) *Attorney, Agent, or Firm* — Oliff PLC

(57) ABSTRACT

The prediction system stores a learned model that is machine-learned so as to output a demand prediction result that is a prediction result of the demand of the medical device by inputting electronic medical record data in which information indicating the necessity of use of the medical device is described, using learning data including loan result data indicating a result of lending the medical device and electronic medical record data in which information indicating the necessity of use of the medical device is described. The prediction system acquires a demand prediction result by inputting the electronic medical record data into the learned model, and inputs an inventory prediction result which is a prediction result of the inventory of the medical device, compares the acquired demand prediction result with the input inventory prediction result, and notifies the medical device lending system when the demand exceeds the inventory.

10 Claims, 14 Drawing Sheets

(56) References Cited

U.S. PATENT DOCUMENTS

| | | | | |
|---|---|---|---|---|
| 2009/0144078 | A1* | 6/2009 | Bajars | G16H 40/20 705/2 |
| 2016/0217347 | A1* | 7/2016 | Mineo | A61B 5/441 |
| 2017/0061375 | A1* | 3/2017 | Laster | G16H 20/40 |
| 2019/0172012 | A1* | 6/2019 | Roy | G06Q 10/0875 |
| 2020/0364660 | A1* | 11/2020 | Hines | G16H 20/13 |
| 2021/0174963 | A1* | 6/2021 | Hill, Jr. | G16H 50/20 |
| 2022/0293254 | A1* | 9/2022 | Reynolds | G06F 3/0482 |
| 2023/0307117 | A1* | 9/2023 | Kumar | G16H 40/67 |
| 2024/0058968 | A1* | 2/2024 | Farhat | B25J 19/0054 |

* cited by examiner 1
30
EQUIPMENT LENDING SYSTEM
10
HOST MANAGEMENT DEVICE
40
ELECTRONIC MEDICAL CHART SYSTEM
600
610
610
400
400
U1
U2
20
27, 28
24
25
26
25
24

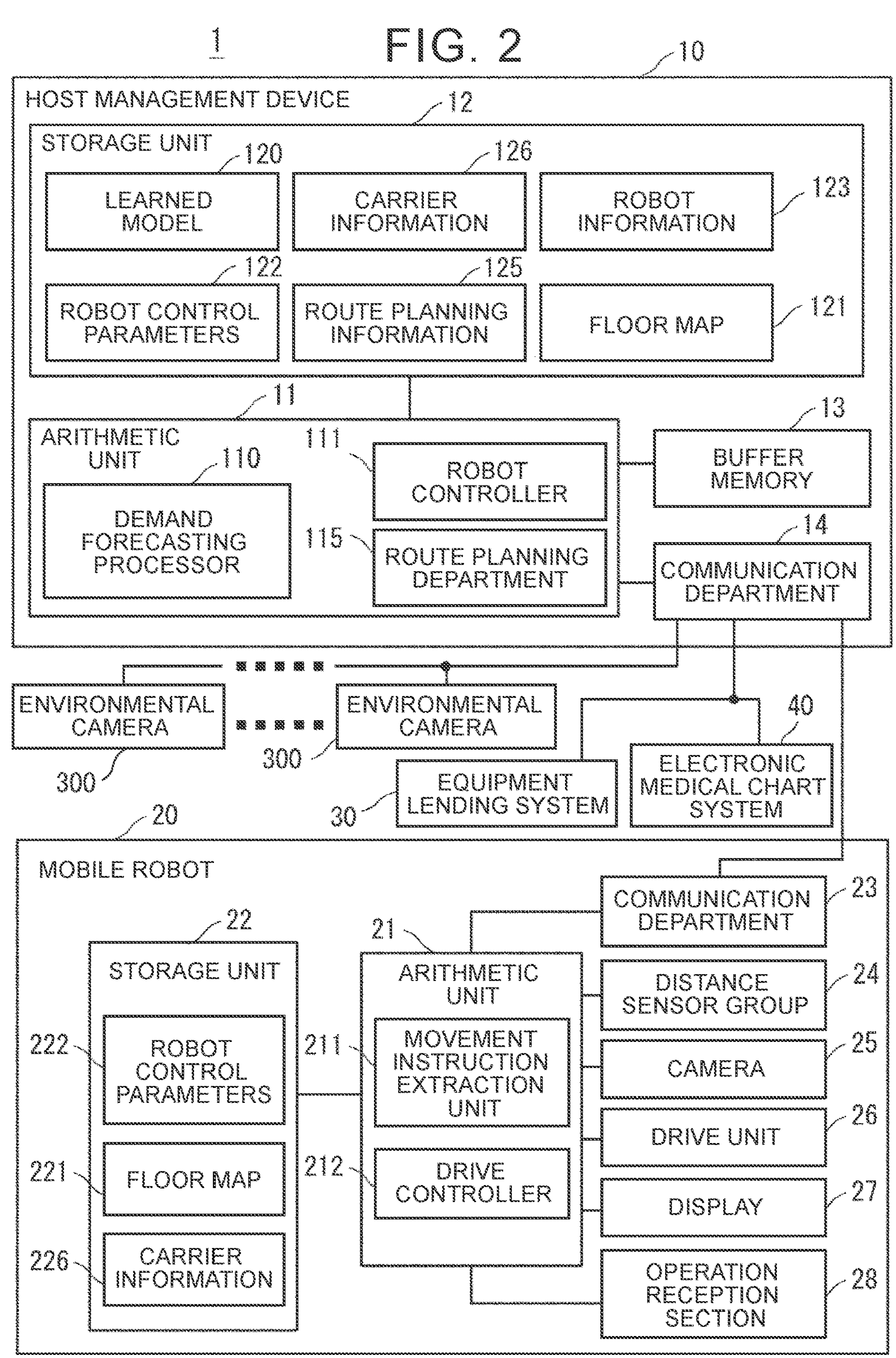
FIG. 2
1
10
HOST MANAGEMENT DEVICE
12
STORAGE UNIT
120
LEARNED MODEL
126
CARRIER INFORMATION
ROBOT INFORMATION
123
122
ROBOT CONTROL PARAMETERS
125
ROUTE PLANNING INFORMATION
FLOOR MAP
121
11
ARITHMETIC UNIT
110
DEMAND FORECASTING PROCESSOR
111
ROBOT CONTROLLER
115
ROUTE PLANNING DEPARTMENT
13
BUFFER MEMORY
14
COMMUNICATION DEPARTMENT
ENVIRONMENTAL CAMERA
300
ENVIRONMENTAL CAMERA
300
EQUIPMENT LENDING SYSTEM
30
40
ELECTRONIC MEDICAL CHART SYSTEM
20
MOBILE ROBOT
22
STORAGE UNIT
222
ROBOT CONTROL PARAMETERS
221
FLOOR MAP
226
CARRIER INFORMATION
21
ARITHMETIC UNIT
211
MOVEMENT INSTRUCTION EXTRACTION UNIT
212
DRIVE CONTROLLER
COMMUNICATION DEPARTMENT
23
DISTANCE SENSOR GROUP
24
CAMERA
25
DRIVE UNIT
26
DISPLAY
27
OPERATION RECEPTION SECTION
28

FIG. 5

| MEDICAL RECORD ID | PATIENT ID | PATIENT NAME | NAME OF DISEASE | LINK FOR DISEASE IMAGES | ACTION | NEED FOR HOSPITALIZATION | DISPOSAL SITE | TREATMENT START TIME | TREATMENT END TIME | PLANNED TREATMENT PERSONNEL |
|---|---|---|---|---|---|---|---|---|---|---|
| 001 | P001 | . . . | DIABETES | . . . | INSULIN MEDICATION | REQUIRED | G001 | 13:00 | 15:30 | U001 |
| 002 | P002 | . . . | LUNG CANCER | . . . | ANTICANCER DRUG ADMINISTRATION | REQUIRED | G002 | 13:50 | 14:00 | U002 |
| . . . | . . . | . . . | . . . | . . . | . . . | . . . | . . . | . . . | . . . | . . . |

FIG. 6

| LENDING CONTROL NUMBER | DEVICE CONTROL NUMBER | NAME | NECESSITY OF MAINTENANCE | MECHANIC TYPE | TRANSPORT DESTINATION (PLACE OF USE) | PROSPECTIVE USERS | START TIME OF USE | END OF USE TIME | OFFICIAL/ TEMPORARY RESERVATIONS |
|---|---|---|---|---|---|---|---|---|---|
| 001 | E001 | SYRINGE PUMP | REQUIRED | MA001 | G001 | U001 | 13:00 | 15:30 | OFFICIAL |
| 002 | E002 | INFUSION PUMP | REQUIRED | MA002 | G001 | U002 | 13:50 | 14:00 | OFFICIAL |
| 003 | E003 | TRANSFUSION PUMP | REQUIRED | MA001 | G002 | U004 | 16:00 | 18:30 | PRELIMINARY RESERVATION |
| . . . | . . . | . . . | . . . | . . . | . . . | . . . | . . . | . . . | . . . |

FIG. 7

| TRANSPORT CONTROL NUMBER | DEVICE CONTROL NUMBER | NAME | NECESSITY OF MAINTE-NANCE | MECHANIC TYPE | TRANSPORT SOURCE | TRANSPORT DESTINATION | PROS-PECTIVE USERS | ROBOTIC ID | STATUS | START TIME OF USE | END OF USE TIME |
|---|---|---|---|---|---|---|---|---|---|---|---|
| 001 | E001 | SYRINGE PUMP | REQUIRED | MA001 | S001 | G001 | U001 | AAA | TRANS-PORTED | 13:00 | 15:30 |
| 002 | E002 | INFUSION PUMP | REQUIRED | MA002 | S001 | G001 | U002 | BBB | TRANS-PORTING | 13:50 | 14:00 |
| ... | ... | ... | ... | ... | ... | ... | ... | ... | ... | ... | ... |

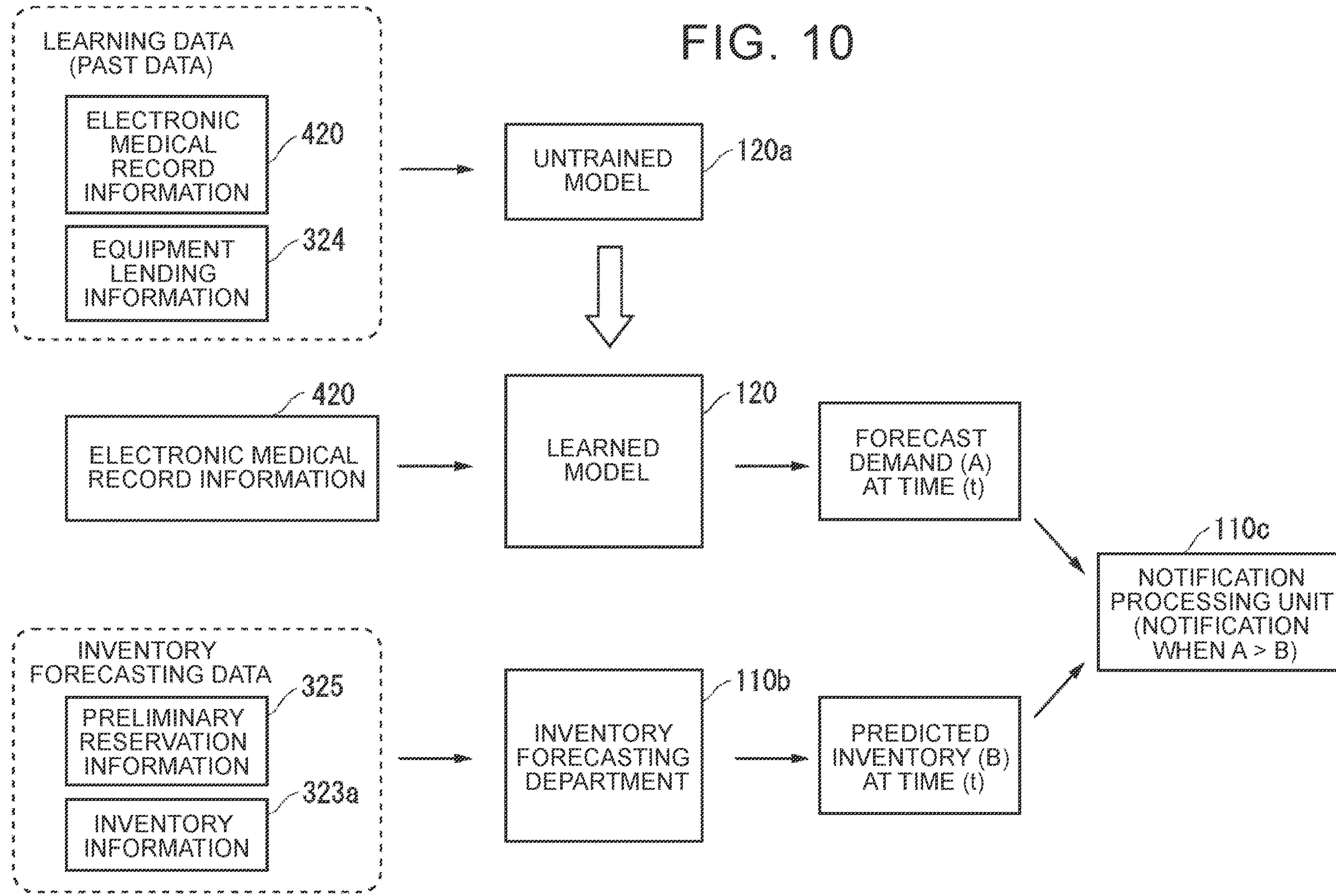
FIG. 10
LEARNING DATA (PAST DATA)
ELECTRONIC MEDICAL RECORD INFORMATION
420
EQUIPMENT LENDING INFORMATION
324
UNTRAINED MODEL
120a
420
ELECTRONIC MEDICAL RECORD INFORMATION
LEARNED MODEL
120
FORECAST DEMAND (A) AT TIME (t)
110c
NOTIFICATION PROCESSING UNIT (NOTIFICATION WHEN A > B)
INVENTORY FORECASTING DATA
PRELIMINARY RESERVATION INFORMATION
325
INVENTORY INFORMATION
323a
INVENTORY FORECASTING DEPARTMENT
110b
PREDICTED INVENTORY (B) AT TIME (t)

FIG. 11

| PATIENT α | | |
|---|---|---|
| MEDICAL DEVICES | SYRINGE PUMP | INFUSION PUMP |
| NUMBER OF UNITS | 1 | 1 |
| ESTIMATED DATE AND TIME OF USE | 2021/10/5 9:00 | 2021/10/5 16:00 |

PREDICTION SYSTEM, PREDICTION METHOD, AND STORAGE MEDIUM

CROSS-REFERENCE TO RELATED APPLICATION

This application claims priority to Japanese Patent Application No. 2022-108331 filed on Jul. 5, 2022, incorporated herein by reference in its entirety.

BACKGROUND

1. Technical Field

The present disclosure relates to a prediction system, a prediction method, and a storage medium.

2. Description of Related Art

Japanese Unexamined Patent Application Publication No. 2021-140273 (JP 2021-140273 A) discloses an information processing device that adjusts a distribution base in accordance with a demand prediction. The information processing device generates product demand information indicating a trend of a demand for a product for each region based on a place where an action of each user related to the product is performed and a number of actions performed at the place, and determines a distribution base of the product based on the product demand information. Further, the information processing device creates a transportation plan for transporting the product to the distribution base of the product in advance based on the product demand information. Furthermore, the information processing device creates an inventory conveyance plan for transferring the inventory of the product to the distribution base of the product in advance from another distribution base where the product is in stock based on the product demand information.

SUMMARY

In a medical device lending system that lends out medical devices, a situation occurs in which inventory is insufficient in a case where a lending demand for medical devices rapidly increases. Therefore, it is desired to predict the lending demand for medical devices in advance in order to make it possible to take measures for securing inventory before the inventory shortage occurs. The technology described in JP 2021-140273 A cannot solve such a problem because the lending demand for medical devices cannot be predicted in advance.

The present disclosure has been made to solve such a problem, and provides a prediction system, a prediction method, a learned model, and a storage medium capable of predicting in advance a demand for a medical device in a medical device lending system, and a learning system, a learning method, and a storage medium capable of generating such a learned model.

A prediction system according to the present disclosure is a prediction system for predicting a demand for a medical device in a medical device lending system. The prediction system: stores a learned model that has undergone machine learning to output a demand prediction result that is a prediction result of the demand for the medical device by inputting electronic chart data describing information showing a necessity of use of the medical device, using learning data including lending record data indicating a record of the medical device that has been lent and the electronic chart data describing information indicating the necessity of the use of the medical device that has been lent; inputs the electronic chart data describing the information indicating the necessity of the use of the medical device into the learned model to acquire the demand prediction result; inputs an inventory prediction result that is a prediction result of an inventory of the medical device, the prediction result being predicted based on a present inventory and reservation information; and compares the acquired demand prediction result with the input inventory prediction result, and notifies the medical device lending system when the demand exceeds the inventory. In the above prediction system, with such a configuration, the demand for the medical device in the medical device lending system can be predicted in advance, and measures for securing the inventory can be taken before the inventory shortage occurs.

The medical device lending system may include a reservation system for temporarily reserving lending of the medical device. The lending record data may include data in which information indicating the medical device temporarily reserved by the reservation system is associated with information indicating a record of actual lending based on a temporary reservation. Accordingly, in the prediction system, it is possible to predict in advance the demand for the medical device in the medical device lending system in response to the temporary reservation in the medical device lending system.

The electronic chart data may include information indicating that medical staff has determined the use of the medical device. Accordingly, in the prediction system, it is possible to more accurately predict the demand for the medical device in advance in consideration of the record of the medical staffs determination of the use of the medical device.

The lending record data may include information indicating an end time or a return time of the use of the medical device. Accordingly, in the prediction system, it is possible to more accurately predict the demand for the medical device in advance in consideration of the end time or the return time of the actual use of the medical device.

A prediction method according to the present disclosure is a prediction method for predicting, by a computer, a demand for a medical device in a medical device lending system. The prediction method includes: storing, by the computer, a learned model that has undergone machine learning to output a demand prediction result that is a prediction result of the demand for the medical device by inputting electronic chart data describing information showing a necessity of use of the medical device, using learning data including lending record data indicating a record of the medical device that has been lent and the electronic chart data describing information indicating the necessity of the use of the medical device that has been lent; inputting, by the computer, the electronic chart data describing the information indicating the necessity of the use of the medical device into the learned model to acquire the demand prediction result; inputting, by the computer, an inventory prediction result that is a prediction result of an inventory of the medical device, the prediction result being predicted based on a present inventory and reservation information; and comparing, by the computer, the acquired demand prediction result with the input inventory prediction result, and notifies the medical device lending system when the demand exceeds the inventory. In the above prediction method, with such processes, the demand for the medical device in the medical device lending system can be predicted in advance, and measures for securing the inventory can be taken before the inventory shortage occurs.

The medical device lending system may include a reservation system for temporarily reserving lending of the medical device. The lending record data may include data in which information indicating the medical device temporarily reserved by the reservation system is associated with information indicating a record of actual lending based on a temporary reservation. Accordingly, in the prediction system, it is possible to predict in advance the demand for the medical device in the medical device lending system in response to the temporary reservation in the medical device lending system.

The electronic chart data may include information indicating that medical staff has determined the use of the medical device. Accordingly, in the prediction system, it is possible to more accurately predict the demand for the medical device in advance in consideration of the record of the medical staffs determination of the use of the medical device.

The lending record data may include information indicating an end time or a return time of the use of the medical device. Accordingly, in the prediction system, it is possible to more accurately predict the demand for the medical device in advance in consideration of the end time or the return time of the actual use of the medical device.

In a storage medium according to the present disclosure, a program causes a computer to execute a prediction process for predicting a demand for a medical device in a medical device lending system. The prediction process: stores a learned model that has undergone machine learning to output a demand prediction result that is a prediction result of the demand for the medical device by inputting electronic chart data describing information showing a necessity of use of the medical device, using learning data including lending record data indicating a record of the medical device that has been lent and the electronic chart data describing information indicating the necessity of the use of the medical device that has been lent; inputs the electronic chart data describing the information indicating the necessity of the use of the medical device into the learned model to acquire the demand prediction result; inputs an inventory prediction result that is a prediction result of an inventory of the medical device, the prediction result being predicted based on a present inventory and reservation information; and compares the acquired demand prediction result with the input inventory prediction result, and notifies the medical device lending system when the demand exceeds the inventory. In the above program, with such processes, the demand for the medical device in the medical device lending system can be predicted in advance, and measures for securing the inventory can be taken before the inventory shortage occurs.

The medical device lending system may include a reservation system for temporarily reserving lending of the medical device. The lending record data may include data in which information indicating the medical device temporarily reserved by the reservation system is associated with information indicating a record of actual lending based on a temporary reservation. Accordingly, in the prediction system, it is possible to predict in advance the demand for the medical device in the medical device lending system in response to the temporary reservation in the medical device lending system.

The electronic chart data may include information indicating that medical staff has determined the use of the medical device. Accordingly, in the prediction system, it is possible to more accurately predict the demand for the medical device in advance in consideration of the record of the medical staffs determination of the use of the medical device.

The lending record data may include information indicating an end time or a return time of the use of the medical device. Accordingly, in the prediction system, it is possible to more accurately predict the demand for the medical device in advance in consideration of the end time or the return time of the actual use of the medical device.

A learned model according to the present disclosure is a learned model that has undergone machine learning to output a demand prediction result that is a prediction result of a demand for a medical device by inputting electronic chart data describing information showing a necessity of use of the medical device, using learning data including lending record data indicating a record of the medical device that is managed by the medical device lending system and that has been lent and the electronic chart data describing information indicating the necessity of the use of the medical device that has been lent. In the above learned model, with such a configuration, the demand for the medical device in the medical device lending system can be predicted in advance.

A learning system according to the present disclosure is a learning system that inputs learning data including lending record data indicating a record of a medical device that is managed by a medical device lending system and that has been lent and electronic chart data describing information indicating a necessity of use of the medical device that has been lent into a non-learned learning model and executes machine learning to generate a learned model that outputs a demand prediction result that is a prediction result of a demand for the medical device by inputting the electronic chart data describing information indicating the necessity of the use of the medical device. In the above learning system, with such a configuration, it is possible to generate a learned model capable of predicting in advance the demand for the medical device in the medical device lending system.

A learning method according to the present disclosure includes inputting learning data including lending record data indicating a record of a medical device that is managed by a medical device lending system and that has been lent and electronic chart data describing information indicating a necessity of use of the medical device that has been lent into a non-learned learning model and executing machine learning to generate a learned model that outputs a demand prediction result that is a prediction result of a demand for the medical device by inputting the electronic chart data describing information indicating the necessity of the use of the medical device. In the above learning method, with such processes, it is possible to generate a learned model capable of predicting in advance the demand for the medical device in the medical device lending system.

In a storage medium according to the present disclosure, a program causes a computer to execute a learning process including inputting learning data including lending record data indicating a record of a medical device that is managed by a medical device lending system and that has been lent and electronic chart data describing information indicating a necessity of use of the medical device that has been lent into a non-learned learning model and executing machine learning to generate a learned model that outputs a demand prediction result that is a prediction result of a demand for the medical device by inputting the electronic chart data describing information indicating the necessity of the use of the medical device. In the above program, with such processes, it is possible to generate a learned model capable of predicting in advance the demand for the medical device in the medical device lending system.

According to the present disclosure, a prediction system, a prediction method, a learned model, and a storage medium capable of predicting in advance a demand for a medical device in a medical device lending system can be provided, and a learning system, a learning method, and a storage medium capable of generating such a learned model can be provided.

BRIEF DESCRIPTION OF THE DRAWINGS

Features, advantages, and technical and industrial significance of exemplary embodiments of the disclosure will be described below with reference to the accompanying drawings, in which like signs denote like elements, and wherein:

FIG. 2 is a control block diagram illustrating an example of the transport system according to the present embodiment;

FIG. 5 is a table showing an example of electronic medical record information stored in the electronic medical record system of FIG. 4;

FIG. 6 is a table illustrating an example of device lending information and temporary reservation information stored in the device lending system of FIG. 3;

FIG. 7 is a table showing an example of the conveyed object information stored in the host management device of FIG. 2;

FIG. 10 is a schematic diagram for explaining an example of a demand prediction process in the host management device of FIG. 2;

FIG. 11 is a diagram illustrating an example of a demand prediction result output in the demand prediction process of FIG. 10;

DETAILED DESCRIPTION OF EMBODIMENTS

Hereinafter, the present disclosure will be described through embodiments of the disclosure, but the disclosure according to the claims is not limited to the following embodiments. Moreover, all of the configurations described in the embodiments are not necessarily indispensable as means for solving the issue.

EMBODIMENT

Schematic Configuration

The prediction system according to the present embodiment is a system for predicting a demand for a medical device in a medical device lending system, and predicts a demand using a learned model. The learned model is a model that is machine-learned so as to output a demand prediction result by inputting electronic medical record data using learning data including loan result data and electronic medical record data, which will be described in detail later.

Then, the prediction system inputs the electronic medical record data to the learned model to obtain a demand prediction result, and also inputs an inventory prediction result which is a prediction result of the inventory of the medical device predicted based on the current inventory and the reservation information. The reservation system compares the acquired demand prediction result with the input inventory prediction result, and notifies the medical device lending system when the demand exceeds the inventory.

In this prediction system, with this configuration, the demand for the medical device in the medical device lending system can be predicted in advance, and measures for securing the inventory can be taken before the inventory becomes insufficient.

Figure 1:
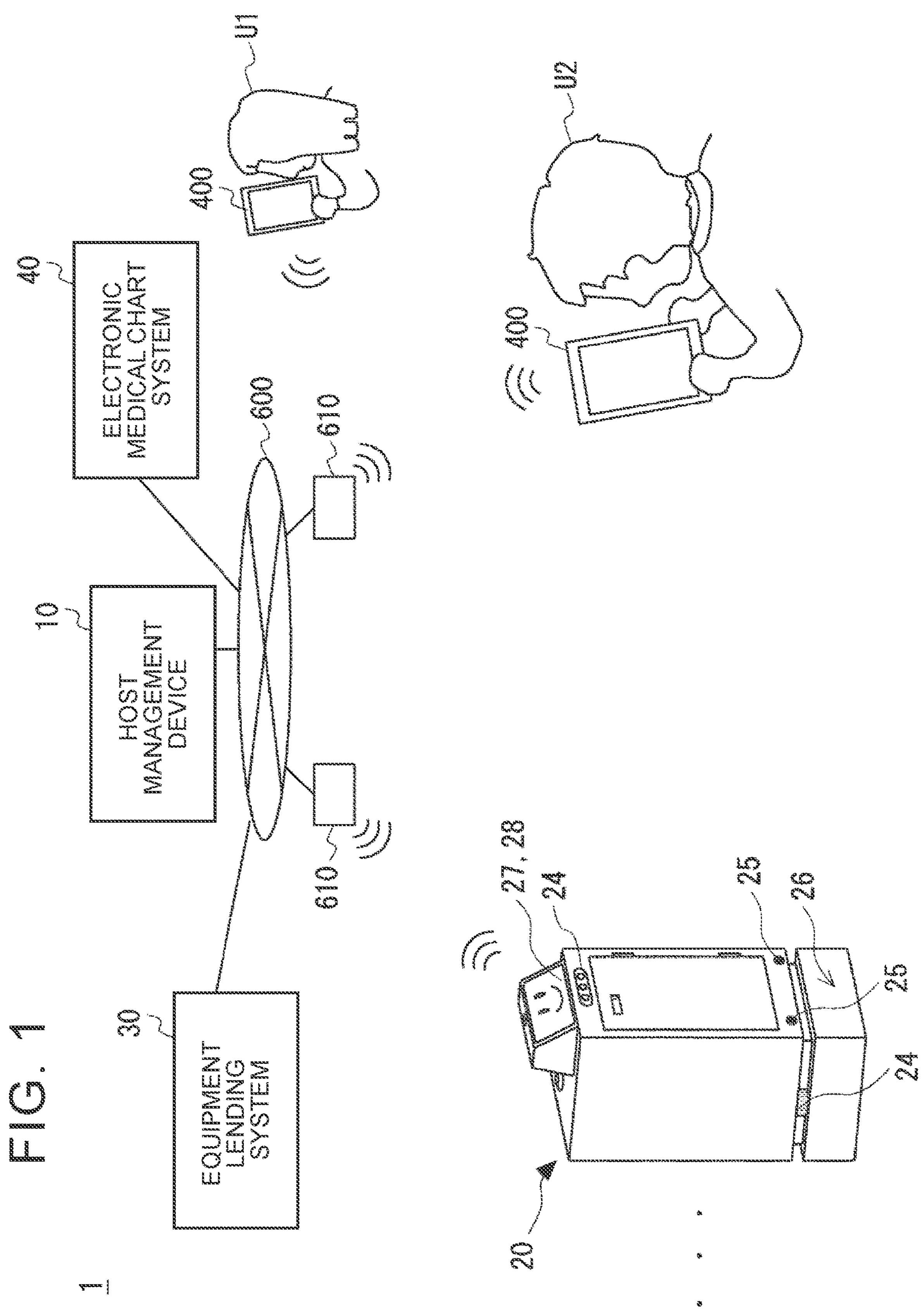
FIG. 1 is a conceptual diagram for describing an overall configuration example of a transport system including a prediction system and a device lending system according to the present embodiment.

First, an example of a transport system using a mobile robot that can incorporate the prediction system according to the present embodiment will be described. FIG. 1 is a conceptual diagram for explaining an overall configuration example of a transport system 1 including a prediction system and a device lending system according to the present embodiment. The transport system 1 according to the present embodiment is a system that transports a conveyed object by using a mobile robot capable of autonomous movement. Although a mobile robot 20 as illustrated in FIG. 1 is described as an example of the mobile robot, the configuration and shape of the mobile robot 20 are not limited thereto.

The transport system 1 includes, in addition to the mobile robot 20, a host management device 10, a medical device lending system (hereinafter referred to as a device lending system) 30, an electronic medical record system 40, a network 600, a communication unit 610, and a user terminal 400.

The mobile robot 20 is a transport robot that executes transportation of a transported object as a task. The mobile robot 20 autonomously travels in order to transport a transported object in a medical welfare facility such as a hospital, a rehabilitation center, a nursing facility, and an elderly care facility. The mobile robot 20 may be a mobile robot that autonomously moves with reference to a map. In addition, the mobile robot 20 can be a mobile robot that autonomously moves a preset region as a region of a part or all of the above-described map, a region indicated by latitude and longitude, or the like. However, the mobile robot 20 can be configured to be able to move autonomously while sensing its surroundings even outside the preset area, outside the entire area included in the map in the first place, or even in a mode in which the movement range is not set, for example.

A user U1 such as a user of the conveyed object, a user assistant, or an administrator of the conveyed object requests the mobile robot 20 to convey the conveyed object. The user U1 stores the conveyed object in the mobile robot 20 at the request location at the time of the conveyance request or at the reception destination (conveyance source) included in the conveyance request information. Of course, the accommodation of the conveyed object can also be carried out by a robot or the like for accommodation. It is to be noted that a mobile robot that is mounted and transported in a state in which the conveyed object is exposed can be adopted, but it is assumed that the conveyed object is transported in a state in which the conveyed object is accommodated in the mobile robot 20 for simplification of explanation.

In the present embodiment, it is only necessary to be able to convey a device to be lent (hereinafter referred to as a lending device) as a conveyed object. However, in the mobile robot 20, a consumable item such as a medicine or a packaging bag, or a transported item other than a lending device or a device, such as a specimen, a hospital meal, a stationery, or the like, may be transported.

The user U1 may request the conveyance of the lending device according to a schedule of the lending (lending schedule). As will be described later, the lending schedule can be managed by the device lending system 30, can be referred to by the user terminal 400 for a transport request by the user U1, and can also be referred to by the host management device 10.

The mobile robot 20 autonomously moves to the set destination and transports the rental device. That is, the mobile robot 20 executes a luggage transport task (hereinafter also simply referred to as a task). In the following description, it is assumed that a location where a lending device is mounted is a conveyance source, and a location where a lending device is reported is a conveyance destination.

For example, it is assumed that the mobile robot 20 moves in a general hospital having a plurality of clinical departments. The mobile robot 20 transports rental equipment among a plurality of clinical departments. For example, the mobile robot 20 delivers a rental device from a nurse station of one clinical department to a nurse station of another clinical department. Alternatively, the mobile robot 20 delivers the rental equipment from its storage to the nurse station of the clinical department. In addition, in a case where the conveyance destination is located on a different floor, the mobile robot 20 may move using an elevator or the like.

Examples of lending devices include medical devices such as inspection devices and medical devices. Examples of the medical device include a bed slip prevention device, a blood pressure monitor, a blood transfusion pump, an infusion device such as a syringe pump, a foot pump, a nurse call, a bed leaving sensor, a foot pump, a low-pressure continuous inhaler, an electrocardiogram monitor, a medicinal product infusion controller, an enteral feeding pump, a ventilator, a cuff pressure gauge, a touch sensor, an aspirator, a nebulizer, a pulse oximeter, a blood pressure gauge, a resuscitator, a sterile device, and an echo device. In addition to these, various types of infusion devices, various types of vital monitors, and the like are also included as medical devices. Note that a plurality of models may be lent to each of various types of medical devices, for example, a pump having a different flow rate is also a target of lending.

In addition, some rental equipment is provided with a stand on its own. For example, such a lending device with a stand includes a low-pressure continuous aspirator, an echo device, an electrocardiogram monitor (transmitter), an electrocardiogram monitor (central monitor), an electrocardiogram monitor (bedside monitor), a ventilator, a nebulizer, and the like. Loan equipment with a stand is often operated by connecting to a commercial power source instead of a battery, and a loan warehouse is often stored as a storage place in comparison with a loan equipment without a stand.

It should be noted that the above-described lending equipment is not required until the sterilization of the main body, or only a part of the equipment needs to be disinfected, and some of the lending equipment is equipped with disposable equipment. Catheters, knife knives, scissors, and the like requiring sterilization can also be handled as lending equipment in the present embodiment when the storage location matches or is close to the location where sterilization is performed.

In the present embodiment, as shown in FIG. 1, the device lending system the electronic medical record system 40, the mobile robot 20, and the user terminal 400 are connected to the host management device 10 via the network 600. The mobile robot 20 and the user terminals 400 are connected to the network 600 via the communication units 610. The network 600 is a wired or wireless local area network (LAN) or wide area network (WAN). The host management device 10 is connected to the network 600 by wire or wirelessly. The communication unit 610 is, for example, a wireless LAN unit installed in each environment. The communication unit 610 may be a general purpose communication device such as a WiFi router.

The user terminal 400 is, for example, a tablet computer, a smartphone, or the like, but may be an installation-type computer. The user terminal 400 only needs to be an information processing device capable of wireless or wired communication.

The user U1 or the user U2 can make a transport request using the user terminal 400. For example, the user U1 can access the device lending system 30 for a transport request from the user terminal 400 (which may be via the host management device 10), and can make a transport request for the lending device to the host management device 10 based on the referred result. The host management device 10 that has received the transfer request can perform the transfer request to the mobile robot 20.

As described above, various types of signals transmitted from the user terminal 400 of the user U1, U2 can be once transmitted to the host management device 10 via the network 600, and can be transferred from the host management device 10 to the target mobile robot 20. Similarly, various signals transmitted from the mobile robot 20 are once sent to the host management device 10 via the network 600, and transmitted from the host management device 10 to the target user terminal 400.

The host management device 10 is a server connected to each equipment, and collects data from each equipment. The host management device 10 is not limited to a physically single device, and may include a plurality of devices that performs distributed processing. Further, the host management device 10 may be distributed and arranged in an edge device such as the mobile robot 20. For example, a part or all of the transport system 1 may be mounted on the mobile robot 20.

The device lending system 30 is a system that manages a lending schedule (management information) indicating a lending date and time and a lending destination (a use place, a user, or the like) for each of the lending devices. The device lending system 30 may be a server connected to the host management device 10, and exchanges data with the host management device 10. Thus, the host management device 10 can obtain the lending schedule of the lending device managed by the device lending system 30. The device lending system 30 may be distributed and arranged in the host management device 10, or may be installed in the host management device 10.

The electronic medical record system 40 is a system that stores and manages electronic medical record data including information on a patient (also referred to as patient information). For example, when a medical practitioner such as a doctor or a nurse inputs patient information using the user terminal 400, the patient information is stored in a memory or the like of the electronic medical record system 40. Further, the medical personnel can view and update the patient information stored in the electronic medical record system 40 through the user terminal 400.

The electronic medical record system 40 may be a server connected to the host management device 10, and exchanges data with the host management device 10. As a result, the host management device 10 can obtain electronic medical record data managed by the electronic medical record system 40. The electronic medical record system 40 may be distributed and arranged in the host management device 10, or may be incorporated and arranged in the host management device 10.

The host management device 10 may be configured to read the medical condition, the operation schedule, and the like from the electronic medical record data registered in the electronic medical record system 40, determine the devices necessary for them, and register the lending of the lending devices, other accessories, and the like in the device lending system 30.

The user terminal 400 and the mobile robot 20 may transmit and receive signals without the host management device 10. For example, the user terminal 400 and the mobile robot 20 may directly transmit and receive signals by wireless communication. Alternatively, the user terminal 400 and the mobile robot 20 may transmit and receive signals via the communication unit 610.

The user U1 or the user U2 uses the user terminal 400 to request conveyance of the rental device. Hereinafter, the description is made assuming that the user U1 is the transport requester at the transport source and the user U2 is the planned recipient at the transport destination (destination). Needless to say, the user U2 at the transport destination can also make a transport request. Further, a user who is located at a location other than the transport source or the transport destination may make a transport request.

When the user U1 makes a conveyance request, the user terminal 400 is used to input the content of the lending device, the recipient of the lending device (hereinafter, also referred to as a conveyance source), the recipient of the lending device (hereinafter, also referred to as a conveyance destination), the scheduled arrival time to the conveyance source (reception time of the lending device), the scheduled arrival time to the conveyance destination (conveyance time limit), and the like. Hereinafter, these types of information are also referred to as transport request information. In the case of a lending device to be transported in the present embodiment, the transportation source may be a storage location (device management location) of the lending device. The conveyance source may be a location where the user U1 is located. The transport destination is a location where the user U2 or a patient who is scheduled to use the transported object is present. The user U1 can input the transport request information by operating the touch panel of the user terminal 400.

Among the conveyance request information, the lending device can be designated by using a lending schedule registered in the device lending system 30. For example, the user U1 designates a rental device from the user terminal 400, and mounts the rental device on the mobile robot 20 as needed, and makes a transfer request to the host management device 10. The host management device 10 that has received the transfer request refers to the device lending system 30, determines the transfer schedule so as to be in time for the use start time indicated by the lending schedule of the lending device, and performs the transfer request to the mobile robot 20, whereby the transfer is performed on the transfer schedule.

Alternatively, the user U1 makes a conveyance request while referring to the lending schedule from the user terminal 400, and the host management device 10 determines the conveyance schedule by referring to the lending schedule, and makes a conveyance request to the mobile robot 20, whereby conveyance is performed on the conveyance schedule. In addition to these, various methods of transportation request can be adopted.

These examples assume that a transfer request is made after a loan schedule is registered based on a loan request (a loan registration request). On the other hand, the lending equipment may be urgently required, and in such a case, the lending schedule for the lending equipment in the required time is not registered. In such cases, the user U1 can also transmit the transport request from the user terminal 400 to the host management device 10. Based on the transfer request, the host management device 10 refers to the device lending system 30 to check whether there is any duplication in the lending period, and if there is no problem, registers it in the lending schedule and makes a transfer request to the mobile robot 20. In this case, loading of the lending device into the mobile robot 20 can be performed, for example, at timings before and after transmission of the transport request from the user terminal 400.

In either case, as described above, the user terminal 400 can transmit the transport request data inputted by the user U1 to the host management device 10. The host management device 10 is a management system that manages a plurality of mobile robots and transmits an operation command for executing a transfer task to each of the mobile robots 20. At this time, the host management device 10 determines the mobile robot 20 that executes the transfer task for each transfer request. The host management device 10 transmits a control signal including an operation command to the mobile robot 20. The mobile robot 20 moves from the transport source so as to arrive at the transport destination in accordance with the operation command.

For example, the host management device 10 assigns a transport task to the mobile robot 20 at or near the transport source. Alternatively, the host management device 10 assigns a transport task to the mobile robot 20 heading toward the transport source or its vicinity. The mobile robot 20 to which the task is assigned goes to take the lending device to the transfer source. The transportation source may be, for example, a storage location or a location where a user U1 requesting a task is located.

When the mobile robot 20 arrives at the transfer source, a user U1 or another staff member places the lending device on the mobile robot 20. A mobile robot 20 equipped with a lending device autonomously moves with a transfer destination as a destination. The host management device 10 transmits a signal to the user terminal 400 of the user U2 at the transport destination. As a result, the user U2 can know that the rental device is being transported and the expected arrival times. When the mobile robot 20 arrives at the set transfer destination, the user U2 can receive the rental device accommodated in the mobile robot 20. In this way, the mobile robot 20 executes the transfer task.

Further, in the overall configuration as described above, each element of the transport system can be distributed to the mobile robot 20, the user terminal 400, the device lending system 30, the electronic medical record system 40, and the host management device 10, and the transport system can be constructed as a whole. In addition, a substantial element for realizing the conveyance of the rental equipment may be assembled in a single device. The host management device 10 controls one or more mobile robots 20.

Control System of the Transport System 1

FIG. 2 is a control block diagram illustrating an example of a control system of the transport system 1. As illustrated in FIG. 2, the transport system 1 may include a host management device 10, a mobile robot 20, a device lending system 30, an electronic medical record system 40, and an environmental camera 300.

The transport system 1 efficiently controls the mobile robots 20 while causing the mobile robots 20 to autonomously move within a predetermined facility. Therefore, a plurality of the environmental cameras 300 is installed in the facility. For example, the environmental cameras 300 are each installed in a passage, a hallway, an elevator, an entrance, etc. in the facility.

The environmental cameras 300 acquire images of ranges in which the mobile robot 20 moves. In the transport system 1, the image acquired by the environmental camera 300 and information based on the image are collected by the host management device 10. Alternatively, the images or the like acquired by the environmental cameras 300 may be directly transmitted to the mobile robots. The environmental cameras 300 may be surveillance cameras or the like provided in a passage or an entrance/exit in the facility. The environmental cameras 300 may be used to determine the distribution of congestion status in the facility.

In the transport system 1, the host management device 10 performs route planning based on the conveyance request information, and generates route planning information. The route planning information may be generated as information obtained by planning a transport route corresponding to the above-described transport schedule. The host management device 10 instructs a destination for each mobile robot 20 based on the generated route planning information. Then, the mobile robot 20 autonomously moves toward the destination designated by the host management device 10. The mobile robot 20 autonomously moves toward the destination using sensors, floor maps, position information, and the like provided in the mobile robot 20 itself.

For example, the mobile robot 20 travels so as not to come into contact with surrounding equipment, objects, walls, and people (hereinafter collectively referred to as peripheral objects). Specifically, the mobile robot 20 detects a distance to a surrounding object. Then, the mobile robot 20 travels in a state of being separated from the surrounding object by a certain distance (a distance threshold value) or more. When the distance from the peripheral object becomes equal to or less than the distance threshold value, the mobile robot 20 decelerates or stops. With this configuration, the mobile robot 20 can travel without coming into contact with the peripheral objects. Since contact can be avoided, safe and efficient transportation is possible.

The host management device 10 may include an arithmetic processing unit 11, a storage unit 12, a buffer memory 13, and a communication unit 14. The arithmetic processing unit 11 performs arithmetic for controlling and managing the mobile robot 20. The arithmetic processing unit 11 can be implemented as, for example, a device capable of executing a program such as a Central Processing Unit (CPU) of a computer. Various functions can also be realized by the program. In FIG. 2, only the characteristic demand prediction processing unit 110, the robot control unit 111, and the route planning unit 115 are shown in the arithmetic processing unit 11, but other processing blocks are also provided.

The demand prediction processing unit 110 inputs, to the learned model 120 stored in the storage unit 12, electronic medical record data in which information indicating the necessity of use of the medical device is described, and acquires a demand prediction result that is a prediction result of the demand of the medical device after a predetermined period of time (for example, a designated date and time) has elapsed from the learned model 120 or at the time of the start of use.

Here, the information indicating the necessity of use of the medical device is information indicating the medical device itself, information indicating an operation necessary for the patient, information indicating a symptom of the patient, information indicating a treatment to the patient, or the like, or information obtained by combining a plurality of pieces of the information.

Further, the demand prediction processing unit 110 inputs an inventory prediction result that is a prediction result of the inventory of the medical device after a predetermined period has elapsed or at the time of the start of use, which is predicted based on the current inventory and the reservation information. Here, the demand prediction processing unit 110 may acquire an inventory prediction result using a learned model for inventory prediction (inventory estimation), which is not illustrated. Further, for example, the demand prediction processing unit 110 may receive, from the device lending system 30, an inventory prediction result obtained by performing such prediction on the device lending system 30 side. The demand prediction result and the inventory prediction result can be obtained for each medical device.

Then, the demand prediction processing unit 110 compares the acquired demand prediction result with the input stock prediction result. When the demand after the predetermined period has elapsed or at the time of the start of use exceeds the inventory, the demand prediction processing unit 110 notifies the device lending system 30 via the communication unit 14. The notification content may include that the demand has exceeded the inventory, the medical device of the subject, the date and time of the exceedance, and the like.

The robot control unit 111 performs arithmetic for remotely controlling the mobile robot 20 and generates a control signal. The robot control unit 111 generates a control signal based on the route planning information 125 and the like, which will be described later. Further, the robot control unit 111 generates a control signal based on various types of information obtained from the environmental cameras 300 and the mobile robots 20. The control signal may include update information such as a floor map 121, robot information 123, and a robot control parameter 122, which will be described later. That is, when various types of information are updated, the robot control unit 111 generates a control signal in accordance with the updated information.

The route planning unit 115 performs route planning for each mobile robot 20. When the transport task is input, the route planning unit 115 performs a route plan for transporting the rental device to the transport destination based on the transport request information. Specifically, the route planning unit 115 refers to the route planning information 125, the robot information 123, and the like that are already stored in the storage unit 12, and determines the mobile robot 20 that executes the new transport task.

The departure point is the current position of the mobile robot 20, the transfer destination of the immediately preceding transfer task, the receiving destination of the lending device, and the like. The destination is a conveyance destination of the rental device, but may be a standby location, a charging location, or the like. Here, the route planning unit 115 sets passing points from the starting point to the destination of the mobile robot 20. The route planning unit 115 sets the passing order of the passing points for each mobile robot 20. The passing points are set, for example, at branch points, intersections, lobbies in front of elevators, and their surroundings. In a narrow passage, it may be difficult for the mobile robots 20 to pass each other. In such a case, a passage having a narrow width may be set as a passing point in front of the passage. Candidates for the passing points may be registered in the floor map 121 in advance.

The route planning unit 115 determines the mobile robot 20 that performs each transport task from among the mobile robots 20 such that the entire system can efficiently execute the task. The route planning unit 115 preferentially assigns the transport task to the mobile robot 20 on standby and the mobile robot 20 close to the transport source.

The route planning unit 115 sets passing points including the starting point and the destination for the mobile robot 20 to which the transport task is assigned. For example, when there are two or more movement routes from the transport source to the transport destination, the passing points are set such that the movement can be performed in a shorter time. Thus, the host management device 10 updates the information indicating the congestion status of the passages based on the images of the camera or the like. Specifically, locations where other mobile robots 20 are passing and locations with many people have a high degree of congestion. Therefore, the route planning unit 115 sets the passing points so as to avoid locations with a high degree of congestion.

The mobile robot 20 may be able to move to the destination by either a counterclockwise movement route or a clockwise movement route. In such a case, the route planning unit 115 sets the passing points so as to pass through the less congested movement route. The route planning unit 115 sets one or more passing points to the destination, whereby the mobile robot 20 can move along a movement route that is not congested. For example, when a passage is divided at a branch point or an intersection, the route planning unit 115 sets a passing point at the branch point, the intersection, the corner, and the surroundings as appropriate. Accordingly, the transport efficiency can be improved.

The route planning unit 115 may set the passing points in consideration of the congestion status of the elevator, the moving distance, and the like. Further, the host management device 10 may estimate the number of the mobile robots 20 and the number of people at the estimated time when the mobile robot 20 passes through a certain location. Then, the route planning unit 115 may set the passing points in accordance with the estimated congestion status. Further, the route planning unit 115 may dynamically change the passing points in accordance with a change in the congestion status. The route planning unit 115 sets the passing points sequentially for the mobile robot 20 to which the transport task is actually assigned. The passing points may include the transport source and the transport destination. The mobile robot 20 autonomously moves so as to sequentially pass through the passing points set by the route planning unit 115.

The storage unit 12 is a storage unit that stores information necessary for management and control of the mobile robot 20 and the like. In the example of FIG. 2, the learned model 120, the floor map 121, the robot information 123, the robot control parameter 122, the route planning information 125, and the conveyed object information 126 are shown. However, the information stored in the storage unit 12 may be other than this. The arithmetic processing unit 11 performs an arithmetic operation using information stored in the storage unit 12 when performing various kinds of processing. In addition, various kinds of information stored in the storage unit 12 can be updated to the latest information.

The learned model 120 is a learning model that is machine-learned using learning data including lending record data indicating a result of lending a medical device and electronic medical record data describing information indicating the necessity of use of the lending medical device. Then, the learned model 120 is assumed to be machine-learned so as to input electronic medical record data in which information indicating the necessity of use of the medical device is described, and output a demand prediction result that is a prediction result of the demand of the medical device after the lapse of a predetermined period or at the time of the start of use. That is, the learned model 120 is a model that is an algorithm for predicting a demand prediction result from the electronic medical record data. Regardless of the algorithm or the like, it is sufficient that such prediction is possible. Note that the learned model 120 can be updated at a predetermined timing at which the operation proceeds and data is accumulated.

Here, the loan result data is data indicating a loan result of the medical device to be managed by the device lending system 30. The lending result data can be managed by a storage unit (a storage unit 32 described later) of the device lending system 30. The end of the use of the medical device can be obtained, for example, by the user U2 or the like based on the input from the user terminal 400, and the same applies to the beginning of the use of the medical device. In either case of the end of use or the start of use, the user terminal 400 can transmit the input result to the device lending system 30 directly or via the host management device 10 via the network 600 and record the input result as the lending result data together with the date and time. However, the start and end of the use of the medical device can be obtained by other methods. For example, in a case where the medical device is a device that receives power supply from an outlet, the start and end of use of the medical device are determined based on the power consumption detected by a sensor or the like attached to the outlet of the rental place (use place). The determination result is transmitted to the device lending system 30 directly or via the host management device 10 via the network 600. It can be recorded as loan record data along with the date and time. Alternatively, communication is performed between the medical device side and a predetermined place as a lending place, so that the medical device and the predetermined place are close to each other and separated from each other. Thus, it is determined that the use of each medical device has started and ended. The determination result may be transmitted to the device lending system 30 directly or via the host management device 10 via the network 600, and may be recorded as the lending result data together with the date and time. The communication can be realized by, for example, using a beacon that emits radio waves such as Bluetooth (registered trademark) and Bluetooth Low Energy (registered trademark) and a device that detects the radio waves, or using a Radio Frequency Identification (RFID tag such as a Nearfield communication (NFC) tag and a tag reader thereof. It should be noted that the medical device and the predetermined location may be the originating side and the receiving side, and whether the medical device incorporates such a communication function or the device having such a communication function may be externally attached.

The floor map 121 is map information of a facility in which the mobile robot 20 moves. The floor map 121 may be created in advance. The floor map 121 may be generated from information obtained from the mobile robot 20. In addition, the floor map 121 may be a base map created in advance plus map correction information generated from information obtained from the mobile robot 20.

The robot information 123 indicates the ID, model number, specifications, and the like of the mobile robot 20 managed by the host management device 10. The robot information 123 may include position information indicating the current position of the mobile robot 20. The robot information 123 may include information on whether the mobile robot 20 is executing a task or at standby. Further, the robot information 123 may also include information indicating whether the mobile robot 20 is operating, out-of-order, or the like. Further, the robot information 123 may include information on a transportable lending device and a non-transportable lending device.

The robot control parameter 122 indicates control parameters such as a threshold distance from a peripheral object for the mobile robot 20 managed by the host management device 10. The threshold distance is a margin distance for avoiding contact with the peripheral objects including a person. Further, the robot control parameter 122 may include information on an operation intensity such as a speed upper limit value of a moving speed of the mobile robot 20.

The robot control parameter 122 may be updated depending on the situation. The robot control parameter 122 may include information indicating an empty state or a usage state of the accommodation space in the mobile robot 20. The robot control parameter 122 may include information of a transportable lending device or a non-transportable lending device. Of course, the robot control parameter 122 may also include information indicating the possibility/impossibility of transporting the conveyed object other than the lending device. The above-described various types of information in the robot control parameter 122 are associated with each mobile robot 20.

The route planning information 125 includes the route planning information planned by the route planning unit 115. The route planning information 125 includes, for example, information indicating a transport task. The route planning information 125 may include information such as ID of the mobile robot 20 to which the task is assigned, the departure point, the content of the rental device, the conveyance destination, the conveyance source, the scheduled arrival time to the conveyance destination, the scheduled arrival time to the conveyance source, and the arrival time. In the route planning information 125, the various types of information described above may be associated with each transport task. The route planning information 125 may include at least a part of the conveyance request information inputted from the user U1 or the like.

Further, the route planning information 125 may include information on the passing points for each mobile robot 20 and each transport task. For example, the route planning information 125 includes information indicating the passing order of the passing points for each mobile robot 20. The route planning information 125 may include the coordinates of each passing point on the floor map 121 and information on whether the mobile robot 20 has passed the passing points.

The conveyed object information 126 is information related to the lending device on which the conveyance request is made. For example, it includes information such as the content (type) of the lending device, the conveyance source, and the conveyance destination. Needless to say, the conveyed object information 126 may include information on conveyed objects other than the rental equipment, and the same applies hereinafter to the conveyed object information 126. The conveyed object information 126 may include an ID of the mobile robots 20 in charge of conveyance. Further, the conveyed object information 126 may include information indicating a status such as during conveyance, before conveyance (before mounting), and after conveyance. The conveyed object information 126 is associated with each lending device. The details of the conveyed object information 126 will be described later.

The route planning unit 115 refers to various types of information stored in the storage unit 12 to formulate a route plan. For example, based on the floor map 121, the robot information 123, the robot control parameter 122, and the route planning information 125, the route planning unit 115 determines the mobile robot 20 that executes the task. Then, the route planning unit 115 refers to the floor map 121 and the like to set the passing points to the transport destination and the passing order thereof. Candidates for the passing points are registered in the floor map 121 in advance. The route planning unit 115 sets the passing points in accordance with the congestion status and the like. In the case of continuous processing of tasks, the route planning unit 115 may set the transport source and the transport destination as the passing points.

In addition, two or more mobile robots 20 may be assigned to one transfer task. For example, if the lending device is larger than the transportable capacity of the mobile robot 20, one lending device is divided into two and mounted on the two mobile robots 20. Alternatively, if the lending device is heavier than the transportable weight of the mobile robot 20, one lending device is divided into two and mounted on the two mobile robots 20. With this configuration, one transport task can be shared and executed by two or more mobile robots 20. Of course, in the case of controlling the mobile robots 20 having different sizes, a route plan may be performed so that the mobile robots 20 capable of transporting the rental equipment receive the rental equipment.

Further, one mobile robot 20 may perform two or more transport tasks in parallel. For example, one mobile robot 20 may simultaneously mount two or more lending devices and sequentially transport them to different transport destinations. Alternatively, other lending devices may be mounted while one mobile robot 20 is transporting one lending device. In addition, the transfer destinations of the lending devices mounted at different locations may be the same or may be different. With this configuration, the tasks can be executed efficiently.

In such a case, storage information indicating the usage status or the availability of the storage space of the mobile robot 20 may be updated. That is, the host management device 10 may manage the storage information indicating the availability and control the mobile robot 20. For example, when the loading or receiving of the lending device is completed, the accommodation information is updated. When the transfer task is input, the host management device 10 refers to the accommodation information and directs the mobile robot 20 having an empty space on which the rental device can be mounted to the reception. With this configuration, one mobile robot 20 can execute a plurality of transport tasks at the same time, and two or more mobile robots 20 can share and execute the transport tasks. For example, a sensor may be installed in the accommodation space of the mobile robot 20 to detect an empty state.

In addition, the capacity and weight of each lending device may be registered in advance.

The buffer memory 13 is a memory that stores intermediate information generated in the processing of the arithmetic processing unit 11. The communication unit 14 is a communication interface for communicating with a plurality of environmental cameras 300, at least one mobile robot 20, and the like provided in a facility in which the transport system 1 is operated. The communication unit 14 can perform both wired communication and wireless communication. For example, the communication unit 14 transmits a control signal necessary for controlling the mobile robot 20 to each of the mobile robots 20 based on an instruction from the arithmetic processing unit 11. In addition, the communication unit 14 can receive information collected by the mobile robot 20 or the environmental camera 300 and pass the information to the arithmetic processing unit 11. In addition, the communication unit 14 can receive information such as a lending schedule from the device lending system 30, pass the information to the arithmetic processing unit 11, and transmit information such as a lending schedule to the device lending system 30 for registration based on an instruction from the arithmetic processing unit 11. Further, the communication unit 14 can receive the electronic medical record information from the electronic medical record system 40 and pass the electronic medical record information to the arithmetic processing unit 11.

The mobile robot 20 may include an arithmetic processing unit 21, a storage unit 22, a communication unit 23, a proximity sensor (for example, a distance sensor group 24), a camera 25, a drive unit 26, a display unit 27, and an operation reception unit 28. Although FIG. 2 shows only typical processing blocks provided in the mobile robot 20, the mobile robot 20 also includes many other processing blocks that are not shown.

The communication unit 23 is a communication interface for communicating with the communication unit 14 of the host management device 10. The communication unit 23 communicates with the communication unit 14 using, for example, a wireless signal. The distance sensor group 24 is, for example, a proximity sensor, and outputs proximity object distance information indicating a distance from an object or a person that is present around the mobile robot 20. The distance sensor group 24 may include, for example, a front-rear distance sensor and a left-right distance sensor, and may measure a distance of a peripheral object in the front-rear direction and a distance of a peripheral object in the left-right direction of the mobile robot 20.

The camera 25, for example, captures an image for grasping the surrounding situation of the mobile robot 20. The camera 25 captures an image of, for example, a forward direction in the traveling direction of the mobile robot 20. The camera can also capture an image of a position marker provided on the ceiling or the like of the facility, for example. The mobile robot 20 may be made to grasp the position of the mobile robot 20 itself using this position marker.

The drive unit 26 drives drive wheels provided on the mobile robot 20. Note that, the drive unit 26 may include an encoder or the like that detects the number of rotations of the drive wheels and the drive motor thereof. The own position (current position) may be estimated in accordance with the output of the encoder. The mobile robot detects its current position and transmits the information to the host management device 10.

The display unit 27 and the operation reception unit 28 are realized by a touch panel display. The display unit 27 displays a user interface screen that serves as the operation reception unit 28. Further, the display unit 27 may display information indicating the destination of the mobile robot 20 and the state of the mobile robot 20. The operation reception unit 28 receives an operation from the user. The operation reception unit 28 includes various switches provided on the mobile robot 20 in addition to the user interface screen displayed on the display unit 27.

The arithmetic processing unit 21 performs arithmetic used for controlling the mobile robot 20. The arithmetic processing unit 21 can be implemented as, for example, a program-executable device such as a central processing unit (CPU) of a computer. Various functions can also be realized by the program. The arithmetic processing unit 21 includes a movement command extraction unit 211 and a drive control unit 212. Although FIG. 2 shows only typical processing blocks included in the arithmetic processing unit 21, the arithmetic processing unit 21 includes processing blocks that are not shown. The arithmetic processing unit 21 may search for a route between the passing points.

The movement command extraction unit 211 extracts a movement command from the control signal given by the host management device 10. For example, the movement command includes information on the next passing point. For example, the control signal may include information on the coordinates of the passing points and the passing order of the passing points. The movement command extraction unit 211 extracts these types of information as a movement command.

Further, the movement command may include information indicating that the movement to the next passing point has become possible. When the passage width is narrow, the mobile robots 20 may not be able to pass each other. In addition, the mobile robot 20 may be temporarily unable to pass through the passage. In such a case, the control signal includes a command to stop the mobile robot 20 at a passing point before the location at which the mobile robot 20 should stop. Then, after the other mobile robot 20 passes or after the mobile robot 20 becomes able to pass, a control signal indicating that the host management device 10 has become able to move to the mobile robot 20 is output. Thus, the mobile robot 20 that has been temporarily stopped resumes movement.

The drive control unit 212 controls the drive unit 26 such that the drive unit 26 moves the mobile robot 20 based on the movement command given from the movement command extraction unit 211. For example, the drive unit 26 includes drive wheels that rotate in accordance with a control command value from the drive control unit 212. The movement command extraction unit 211 extracts the movement command such that the mobile robot 20 moves toward the passing point received from the host management device 10. The drive unit 26 rotationally drives the drive wheels. The mobile robot 20 autonomously moves toward the next passing point. With this configuration, the mobile robot 20 sequentially passes the passing points and arrives at the transport destination. Further, the mobile robot 20 may estimate its own position and transmit a signal indicating that it has passed through the passing point to the host management device 10. Thus, the host management device 10 can manage the current position and the transportation status of each mobile robot 20.

Here, by analyzing the image data output from the camera 25 and the detection signal output from the distance sensor group 24, the drive control unit 212 can identify the position of the own device and recognize the surrounding object. Then, the drive control unit 212 can control the drive unit 26 so as to move the mobile robot 20 based on the result and the movement command. At this time, the drive control unit 212 can recognize the surrounding object and identify the position of the own device with reference to the floor map 221 and the robot control parameter 222.

The storage unit 22 stores a floor map 221, a robot control parameter 222, and conveyed object information 226. Although only a part of the information stored in the storage unit 22 is illustrated in FIG. 2, information other than the floor map 221, the robot control parameter 222, and the conveyed object information 226 illustrated in FIG. 2 is also included. The floor map 221 is map information of a facility in which the mobile robot 20 moves. The floor map 221 is, for example, data obtained by downloading a part or all of the floor map 121 of the host management device 10. Note that the floor map 221 may be created in advance. Further, the floor map 221 may not be the map information of the entire facility but may be the map information including part of the area in which the mobile robot 20 is scheduled to move.

The robot control parameter 222 is a parameter for operating the mobile robot 20. The robot control parameter 222 includes, for example, the distance threshold value from a peripheral object. Further, the robot control parameter 222 also includes a speed upper limit value of the mobile robot 20.

The conveyed object information 226 includes information related to a lending device, similarly to the conveyed object information 126. Information such as the content (type, i.e., model) of the lending device, the conveyance source, and the conveyance destination can be included. The conveyed object information 226 may include information indicating a status such as during conveyance, before conveyance (before mounting), and after conveyance. The conveyed object information 226 is associated with each lending device. The conveyed object information 226 may include information on a lending device conveyed by the mobile robot 20. Therefore, the conveyed object information 226 is part of the conveyed object information 126. That is, the conveyed object information 226 may not include information conveyed by the other mobile robots 20. The conveyed object information 126 will be described later.

The drive control unit 212 refers to the robot control parameter 222 and stops the operation or decelerates in response to the fact that the distance indicated by the distance information obtained from the distance sensor group 24 has fallen below the distance threshold value. The drive control unit 212 controls the drive unit 26 such that the mobile robot 20 travels at a speed equal to or lower than the speed upper limit value. The drive control unit 212 limits the rotation speed of the drive wheels such that the mobile robot 20 does not move at a speed equal to or higher than the speed upper limit value.

Figure 3:
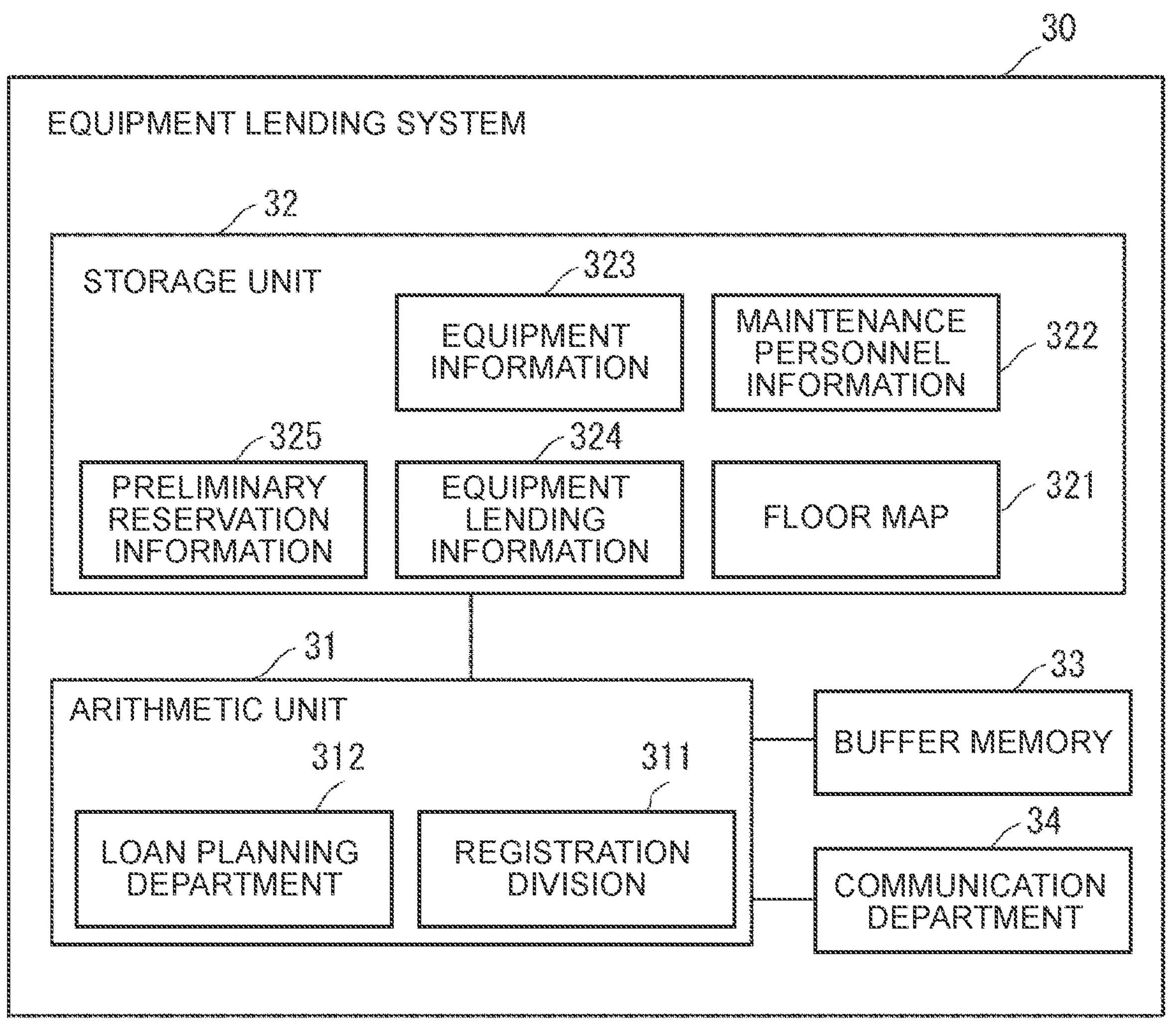
FIG. 3 is a control block diagram illustrating an example of the device lending system of FIG. 2.

FIG. 3 is a control block diagram illustrating an example of the device lending system 30 in the transport system 1 of FIG. 2. As illustrated in FIG. 3, the device lending system 30 may include an arithmetic processing unit 31, a storage unit 32, a buffer memory 33, and a communication unit 34. The arithmetic processing unit 31 performs an arithmetic operation for generating and managing a schedule of the lending device. The arithmetic processing unit 31 can be implemented as, for example, a program-executable device such as a central processing unit (CPU) of a computer. Various functions can also be realized by the program. In FIG. 3, only the characteristic registration unit 311 and the lending planning unit 312 are illustrated in the arithmetic processing unit 31, but other processing blocks are also provided.

The registration unit 311 receives, via the communication unit 34, the lending request information including ID, the usage starting time, the usage ending time, and the usage location of the lending device, which is transmitted from the user terminal 400 in accordance with the manipulation by the user U1, for example, and receives the registration.

Further, the registration unit 311 receives, via the communication unit 34, the loan provisional reservation information including ID, the usage starting time, the usage ending time, and the usage location of the loan device transmitted from the user terminal 400 according to, for example, an operation by the user U1 with respect to the loan device that performs the provisional reservation, and accepts the provisional registration. Further, the registration unit 311 receives, via the communication unit 34, a formal loan request or a cancellation request for the received provisional registration transmitted from the user terminal 400 in accordance with, for example, an operation by the user U1. However, the function of performing the temporary reservation is not essential.

Based on the loan request information received by the registration unit 311, the lending planning unit 312 refers to the device lending information 324 indicating the already planned loan schedule, the temporary reservation information 325 indicating the already provisionally reserved loan schedule, and the other loan request information and the provisional loan reservation information requested at the same time, considering the cancellation request requested at the same time, and confirming that there is no duplication. Of course, in the determination of duplication, even if the same type of medical device is not subject to lending, it is treated as not being duplicated. If there is no duplication, the lending planning unit 312 generates a lending schedule of the lending device based on the received lending request information, and updates the device lending information 324. In a case where the loan request information received by the registration unit 311 is information that overlaps with the existing loan schedule or the like in time (overlaps with the conveyance time), the lending planning unit 312 performs the next reply. That is, the lending planning unit 312 returns a notification indicating duplication to the transmission source of the lending request information (the user terminal 400 or the host management device 10) via the communication unit 34.

Like the loan request information, the lending planning unit 312 confirms that the loan provisional reservation information received by the registration unit 311 does not overlap with the loan provisional reservation information by referring to the already planned loan schedule or the like based on the loan provisional reservation information. If there is no overlap, the lending planning unit 312 generates a lending schedule of the lending device based on the received lending provisional reservation information, and updates the temporary reservation information 325. Note that the information can be shared by using a flag indicating whether the device lending information 324 and the temporary reservation information 325 are formal loans or temporary reservations, or adding a status indicating this fact in the case of a temporary reservation.

Further, the lending planning unit 312 performs formal registration by moving the target information from the temporary reservation information 325 to the device lending information 324 in response to the formal request for the provisional registration received by the registration unit 311. Further, the lending planning unit 312 deletes the target information from the temporary reservation information 325 in response to the cancellation request for the temporary registration received by the registration unit 311, thereby deleting the temporary reservation. As exemplified by the registration unit 311 and the lending planning unit 312 in the above, the device lending system 30 may include a reservation system that temporarily reserves the lending of the medical device.

The storage unit 32 is a storage unit that stores information necessary for lending management of a lending device and control of the device lending system 30. In the example of FIG. 3, the floor map 321, the maintenance person information 322, the device information 323, the device lending information 324, and the temporary reservation information 325 are illustrated, but the information stored in the storage unit 32 may be other than this. The arithmetic processing unit 31 performs an arithmetic operation using information stored in the storage unit 32 when performing various kinds of processing. Various types of information stored in the storage unit 32 can be updated to the latest information.

The device information 323 is information indicating an ID, a model (model number), a size, a weight, and the like of the lending device, and includes information indicating whether or not the device is being lent (that is, inventory information indicating an inventory status), and may also include information indicating a time required for maintenance and a storage location. At least a part of the device information 323 or all of the device information 323 necessary for transportation can be registered in the host management device 10 as a part of the conveyed object information 126. The inventory information may not be included as a part of the device information 323, and may be included as a part of the device information 323 and may be included as a part of the device lending information 324.

The maintenance person information 322 is information associated with each lending device indicated by the device information 323, and may include information indicating a maintenance person who provides each lending device (such as an ID of the maintenance person himself or herself or information indicating a type of the maintenance person) and information indicating a notification destination to each maintenance person. The maintenance person information 322 may be stored in order to notify the maintenance person of the maintenance after the completion of the lending, although the maintenance may be performed before the next lending. The notification for maintenance can be made via the communication unit 14 when the arithmetic processing unit 11 refers to the maintenance person information 322 and the medical device that needs maintenance is transported to the storage location after use. However, this notification can also be executed by the mobile robot 20. With such a notification, the maintenance person can move to the storage place where the lent medical device is transported, as necessary. At the storage location, for example, a maintenance person such as a user U2 performs maintenance such as inspection, cleaning, and replacement of consumables in preparation for the following use, as needed. Examples of maintenance personnel include clinical laboratory technicians, clinical radiology technicians, occupational therapists, physical therapists, clinical engineers, doctors, nurses, and quasi-nurses, as well as technicians from manufacturers of lending equipment.

The floor map 321 may be part or all of the floor map 121. As described above, the device lending information 324 is information indicating a rental schedule for each rental device generated by the lending planning unit 312, and the temporary reservation information 325 is information indicating a temporary reservation for the rental device. The device lending information 324 and the temporary reservation information 325 will be described later.

The buffer memory 33 is a memory that stores intermediate information generated in the processing in the arithmetic processing unit 31. The communication unit 34 is a communication interface for communicating with the host management device 10, and the communication interface may be configured to also communicate with the user terminal 400, the mobile robot 20, and the electronic medical record system 40. The communication unit 34 can perform both wired communication and wireless communication. For example, the communication unit 34 can receive information such as loan request information and provisional loan reservation information from the host management device 10 or the user terminal 400 and pass the information to the arithmetic processing unit 31, and can transmit information such as a loan schedule to the host management device 10 based on an instruction from the arithmetic processing unit 31.

The communication unit 34 can also receive the electronic medical record information from the electronic medical record system 40 and pass the electronic medical record information to the arithmetic processing unit 31. In this case, the registration unit 311 of the arithmetic processing unit 31 may determine whether or not the medical device needs to be lent for surgery or other procedures based on the received electronic medical record information, and, in a necessary case, may generate the lending request information or the lending provisional reservation information of the medical device and pass the information to the lending planning unit 312.

Here, when the registration unit 311 includes information directly indicating a medical device that needs to be lent in the electronic medical record information at the time of the generation, it is possible to generate the lending request information or the provisional lending reservation information for generating the device lending information 324 from the electronic medical record information. On the other hand, when the information directly indicating such a medical device is not included, the registration unit 311 may select a medical device corresponding to a symptom name or the like in accordance with a predetermined rule, and generate loan request information or loan provisional reservation information. Further, the registration unit 311 can determine whether to generate the loan request information or the provisional loan reservation information in accordance with a predetermined rule, and can generate the provisional loan reservation information in a case where, for example, the period until the treatment is one month ahead, one week ahead, or the like for a predetermined period or more, and in other cases, can generate the loan request information. Alternatively, the registration unit 311 may generate the lending request information for the medical device related to the determined treatment, and may generate the provisional lending reservation information in other cases.

The lending planning unit 312 registers the device lending information 324 or the temporary reservation information 325 based on the loan request information or the provisional loan reservation information received in this manner.

Alternatively, the communication unit 34 may receive, from the electronic medical record system 40, the lending request information, the provisional lending reservation information, and the like of the medical device based on the electronic medical record information, and may pass the information to the arithmetic processing unit 31. In this case, the registration unit 311 of the arithmetic processing unit 31 receives the received loan request information or the loan provisional reservation information, and registers the device lending information 324 or the temporary reservation information 325 based on the information received by the lending planning unit 312.

However, as exemplified by the operation performed by the user U1, the registration by the registration unit 311 can be performed by the doctor, the nurse, or the like making a determination of the necessity and performing the operation.

Figure 4:
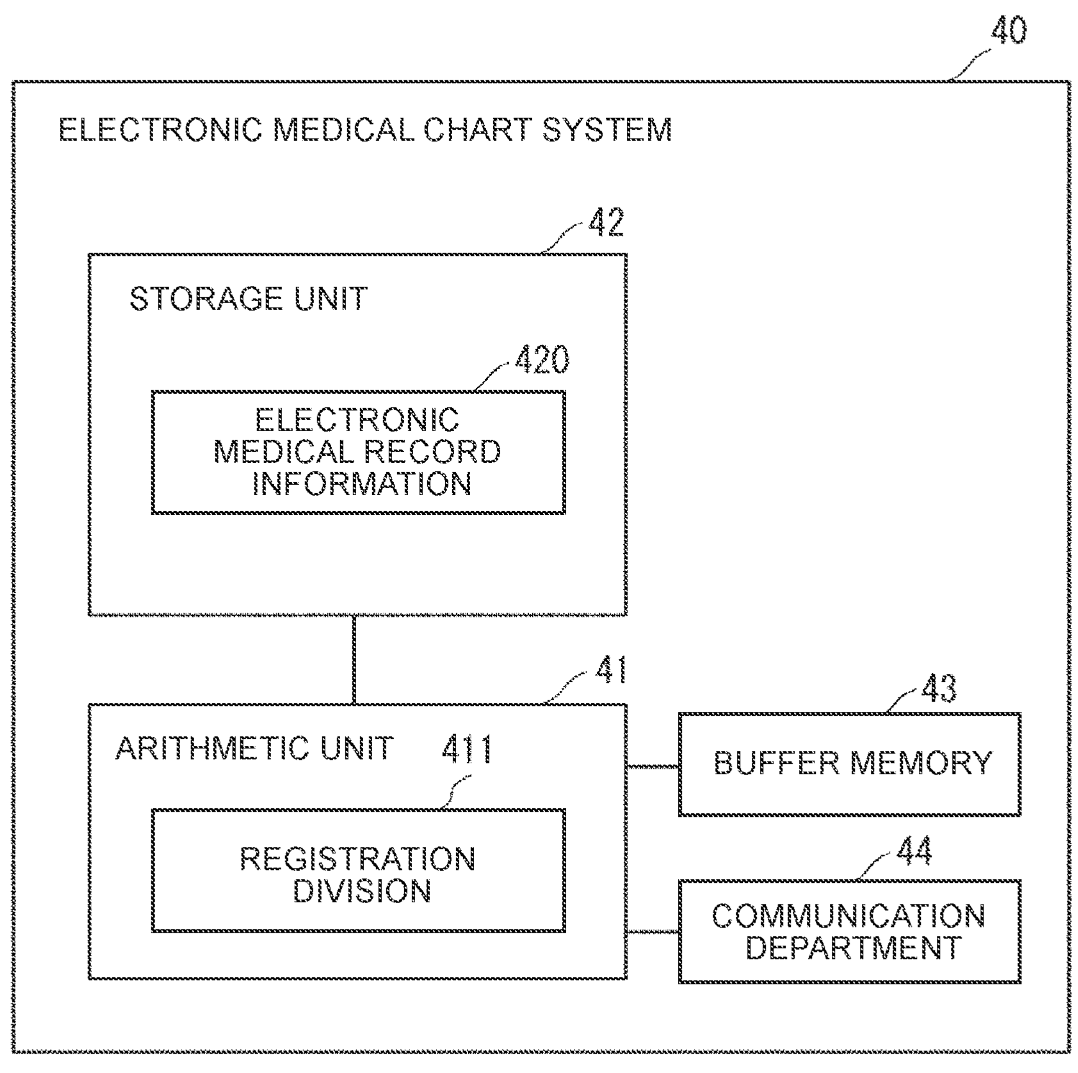
FIG. 4 is a control block diagram illustrating an example of the electronic medical record system of FIG. 2.

FIG. 4 is a control block diagram illustrating an example of the electronic medical record system 40 of FIG. 2. As illustrated in FIG. 4, the electronic medical record system 40 may include an arithmetic processing unit 41, a storage unit 42, a buffer memory 43, and a communication unit 44. The arithmetic processing unit 41 performs an arithmetic operation for generating and managing electronic medical record data. The arithmetic processing unit 41 can be implemented as, for example, a program-executable device such as a central processing unit (CPU) of a computer. Various functions can also be realized by the program. Although only the characteristic registration unit 411 is illustrated in the arithmetic processing unit 41 in FIG. 4, other processing blocks are also provided.

The registration unit 411 receives, via the communication unit 44, medical record registration request information including, for example, a patient's ID, condition, treatment (including surgery), treatment schedule, treatment location, and the like transmitted from the user terminal 400 in accordance with an operation performed by the user U1, accepts registration, and stores the registration as the electronic medical record information 420 in the storage unit 42. The medical record registration request information may include a patient's name, a medical record ID, the necessity or schedule of hospitalization, a staff member or a team of staff members such as a surgeon in the event of an operation, and the like.

The storage unit 42 is a storage unit that stores electronic medical record information 420 to be managed by the electronic medical record system 40 and other information necessary for controlling the electronic medical record system 40. Although the electronic medical record information 420 is illustrated in the example of FIG. 4, the information stored in the storage unit 42 may be other than this. The arithmetic processing unit 41 performs an arithmetic operation using the other information stored in the storage unit 42 when performing various kinds of processing. Various types of information stored in the storage unit 42 can be updated to the latest information.

The electronic medical record information 420 may include information for which registration is requested as medical record registration request information. Note that, among the electronic medical record information 420, for example, a medical record ID, a patient ID, and the like can be automatically attached in accordance with a predetermined rule such as a serial number. The electronic medical record information 420 will be described later.

The buffer memory 43 is a memory that stores intermediate information generated in the processing in the arithmetic processing unit 41. The communication unit 44 is a communication interface for communicating with the host management device 10, and the communication interface may be configured to also communicate with the user terminal 400, the mobile robot 20, and the device lending system 30. The communication unit 44 can perform both wired communication and wireless communication. The communication unit 44 can receive the medical record registration request information from the host management device 10 or the user terminal 400 and pass the received information to the arithmetic processing unit 41, or can transmit the electronic medical record information 420 to the host management device 10 based on an instruction from the arithmetic processing unit 41.

In addition, the communication unit 44 can also transmit, for example, the electronic medical record information 420 or the lending request information, the provisional lending reservation information, and the like of the medical device based on the electronic medical record information 420 to the device lending system 30 based on the instruction from the arithmetic processing unit 41. In the latter case, the arithmetic processing unit 41 refers to the electronic medical record information 420, determines whether or not lending of the medical device is necessary for the operation or other treatment, and when it is necessary, passes an instruction to transmit the lending request information or the provisional lending reservation information of the medical device to the communication unit 44. Here, when the electronic medical record information 420 includes information directly indicating a medical device that needs to be lent, the arithmetic processing unit 41 can generate the lending request information or the provisional lending reservation information for generating the device lending information 324 from the electronic medical record information 420. On the other hand, in a case where the information directly indicating such a medical device is not included, the arithmetic processing unit 41 can select a medical device corresponding to a symptom name or the like according to a predetermined rule and generate loan request information or loan provisional reservation information.

Further, as to which of the lending request information and the provisional loan reservation information is to be generated, the arithmetic processing unit 41 can determine and generate the loan request information in accordance with a predetermined rule, and can generate the temporary loan reservation information in a case where, for example, the period until the treatment is a predetermined period or longer, such as one month or one week ahead, and in other cases, generate the loan request information. Alternatively, the arithmetic processing unit 41 can generate the lending request information for the medical device related to the determined treatment, and can generate the provisional lending reservation information in other cases.

Electronic Medical Record Information 420

FIG. 5 is a table showing an example of the electronic medical record information 420 stored in the electronic medical record system 40 of FIG. 4. As described above, the electronic medical record information 420 may include information for which registration is requested as medical record registration request information. For example, the electronic medical record information 420 may include a medical record ID, a patient ID, a patient name, a condition, a procedure (including an operation, medication, and the like), a procedure schedule, a treatment location, whether or not hospitalization is required, a schedule of treatment, etc. Further, the electronic medical record information 420 may include information indicating a prognosis, that is, information indicating a progress of a symptom after the treatment.

Here, the symptom may include a disease name, an image indicating a position of the disease, and the like. In addition, in the case of an operation, the person to be treated may be a staff member such as a surgeon or a team of staff members. Note that, in FIG. 5, the planned treatment person is exemplified as a user U1, U2 who performs an operation of registering the electronic medical record information 420, that is, is exemplified as a planned user who arranges and collects transportation. However, for the sake of simplicity, the prospective treatment person may be a person different from the prospective user, or the person who performs the registration operation of the electronic medical record information 420 may not be the prospective user or the prospective treatment person. In the example of the table in FIG. 5, a link indicating a storage location of a file indicating this image is described. The electronic medical record information 420 is not limited to the example of FIG. 5, and may include information to be included in a normal medical record. Further, the electronic medical record information 420 may include information directly indicating a medical device when the medical device is required for surgery or other procedures.

Device Lending Information 324, Temporary Reservation Information 325, and Conveyed Object Information 126

Figure 8:
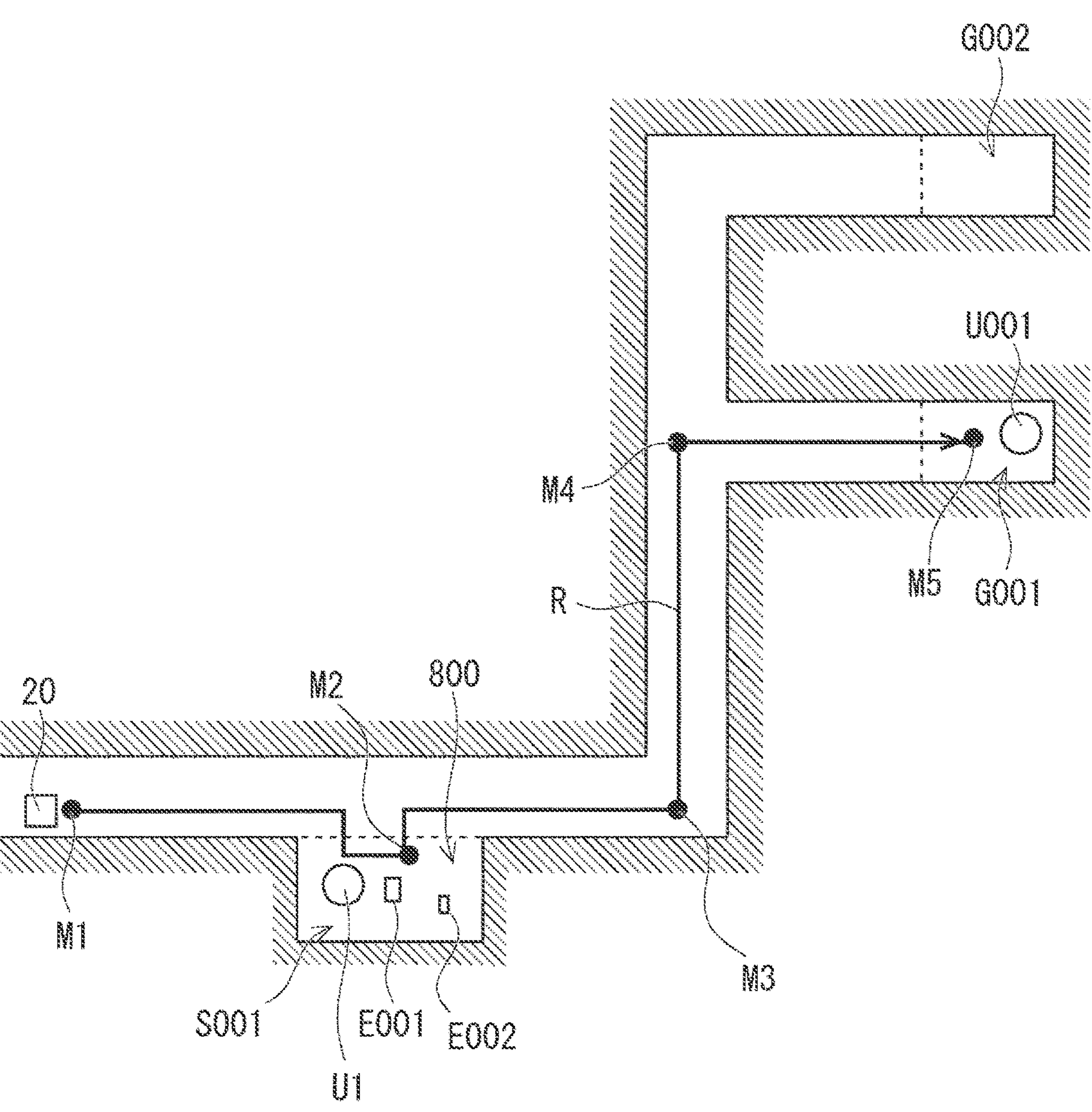
FIG. 8 is a diagram illustrating an example of a moving path of a mobile robot.
Figure 9:
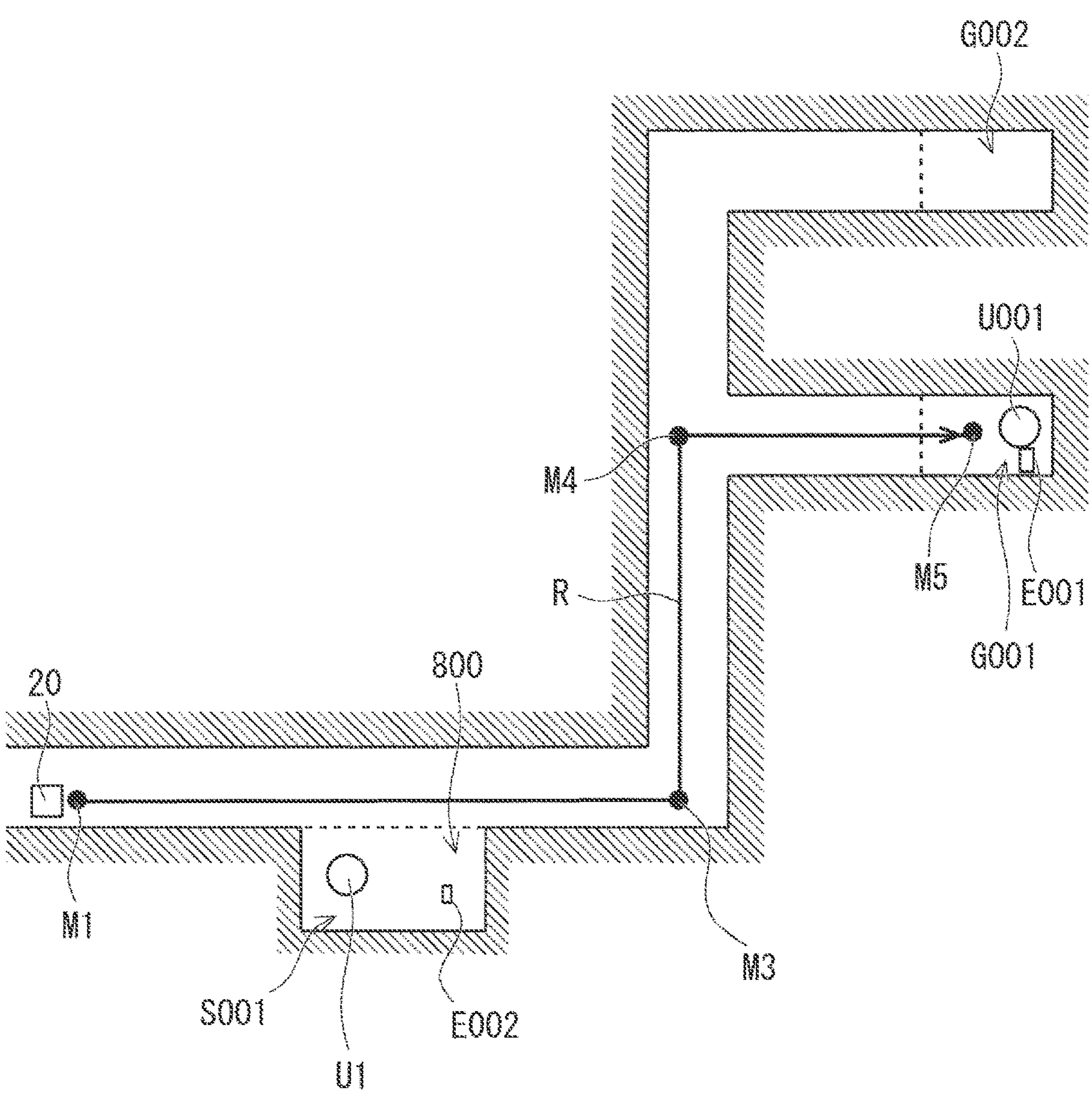
FIG. 9 is a diagram illustrating another example of a moving path of the mobile robot.

An example of the processing of the transport system 1 according to the present embodiment will be described by taking as an example a case where the information illustrated in FIG. 6 is stored as the device lending information 324 and the temporary reservation information 325. FIG. 6 is a table showing an example of the device lending information 324 and the temporary reservation information 325, and FIG. 7 is a table showing an example of the conveyed object information 126. FIG. 8 and FIG. 9 are diagrams illustrating an example of a moving path of the mobile robot.

As illustrated in FIG. 6, the device lending information 324 and the temporary reservation information 325 may include an ID (device control number) of the rental device, a name, necessity of maintenance, a maintenance person type (or maintenance person), a transportation destination (use location), a scheduled user, a use starting time, and a use ending time, as well as information indicating whether formal loan or temporary reservation is made. As illustrated in FIG. 6, these pieces of information can be linked by a loan management number and managed as a table. Note that the distinction between the device lending information 324 and the temporary reservation information 325 can be made by information indicating whether a formal loan or a temporary reservation is made.

The conveyance destination indicates a notification destination (use location) of the loan device, and can be extracted from the loan request information together with the use start time and the use end time. The prospective user indicates a person who uses the rental equipment. For example, the expected user may be the name or ID of the subject, or the name or ID of a staff member such as a nurse, doctor, or the like. Of course, the prospective user may include information of both the patient and the personnel. Information on the necessity of maintenance and information on the type of maintenance person (or maintenance person) may be information indicating whether or not maintenance is required for the respective lending equipment (in this case, essential or optional), or information indicating the type of maintenance person in the case of maintenance (or information indicating ID and name of the maintenance person).

As described above, the device lending information 324 and the temporary reservation information 325 are generated based on the lending request information and the lending temporary reservation information, respectively, and are generated by referring to the device information 323 and the maintenance person information 322 at this time. Note that the information of the maintenance person type or the maintenance person in the maintenance person information 322 or the device lending information 324 is necessary when the maintenance person is notified, and thus is not necessary in an example in which the notification is not performed.

As illustrated in FIG. 7, the conveyed object information 126 may include a device management number, a name, necessity of maintenance, a maintenance person type (or maintenance person) indicating a notification destination, a conveyance source, a conveyance destination, a scheduled user, a robot ID in charge of conveyance, a status, a use starting time, and a use ending time. The conveyed object information 126 does not include information corresponding to the temporary reservation information 325. As illustrated in FIG. 7, these pieces of information can be linked by a transport management number and managed as a table.

The transfer source indicates a location where the mobile robot 20 is to mount the lending device. The conveyance destination indicates a notification destination (use place) of the loan device. Note that, although an example is given in which one storage place is used as the conveyance source, it is needless to say that the storage place is not limited to one place, and the conveyance destination is not limited to two places. The prospective user indicates a person who uses the rental equipment. For example, the expected user is the name or ID of the subject. Alternatively, the prospective user may be the name or ID of a staff member such as a nurse or a doctor. Of course, the prospective user may include information of both the patient and the personnel.

As described above, the conveyed object information 126 is generated based on the conveyance request information. Thus, the conveyed object information 126 can be generated based on information including the device lending information 324 (and information about other conveyed objects) and the mobile robot 20 determined based on the information in consideration of the execution efficiency of the task. The robot ID serves as an ID of the mobile robot 20 that is responsible for transporting the lending device. The robot ID is set based on the route planning considering the performance of the task. The status is information indicating whether the lending device is in the pre-conveyance state, the conveyance state, or the conveyance state. The status is updated at the time when the mobile robot 20 mounts the lending device and at the time when the receipt of the lending device is completed.

Then, the conveyed object information 126 is transmitted to each of the mobile robots 20 in charge of conveyance of the lending device. For example, the conveyed object information 226 of the mobile robot 20 includes information related to a lending device in charge of conveyance by the mobile robot 20. That is, the conveyed object data of the rental device having the robot ID “BBB” may not be transmitted to the mobile robot 20 having the robot ID “AAA”.

Referring to FIGS. 8 and 9, the conveyance of the lending device E001 of FIGS. 6 and 7 will be described. In FIG. 6 and FIG. 7, for the sake of convenience, the time display is set as the day, but it is actually managed by the date and time (date and time). This is because, for example, some devices are rented out over several days or months. In order to initiate transportation from the storage location 800 (S001), FIG. 7 shows an exemplary route setting. Further, the route itself is determined by the route planning unit 115 as described above, and is set in the corresponding mobile robot 20.

With respect to the transfer control number 001, as illustrated in FIG. 8, the mobile robot 20 (robot ID: AAA) first moves from the passing point M1 indicating the current point in time toward the passing point M2 which is the storage location 800 of the lending device E001. After that, the mobile robots 20 receive the lending device E001 at the storage location 800, and then move the passing-point M3, M4 in order to become the route R that goes to the transfer destination G001 (M5). In the transfer destination G001, the scheduled user U001 receives the lending device E001. It should be noted that the mobile robot 20 can then move as needed for other tasks.

The lending device E001 is to be used up to the end-of-use period of 15:30 at the transfer destination G001. Thereafter, the lending device E001 is returned, but since the lending device E001 is a device requiring maintenance, the return destination can be, for example, the storage location 800. It should be noted that the lending equipment that does not require maintenance or is optional may be transported to the next transport destination and used.

When returning the lending device E001, another mobile robot 20 (for example, a robot ID: BBB) can be used. Then, as illustrated by the route R in FIG. 9, the mobile robot 20 moves from the passing-point M1 indicating the current point in time toward the lending device E001 use location G001 and receives the lending device E001 at the use location G001. In the use location G001, a user such as a scheduled user U001 mounts the lending device E001 on the mobile robot 20. After receiving the lending device E001, the mobile robot 20 returns to the storage location 800. It should be noted that the mobile robot 20 can then move as needed for other tasks. The same applies to the transfer and return of the lending device E002 and other lending equipment in FIGS. 6 and 7.

Demand Prediction Processing of this Embodiment

Referring to FIGS. 10 and 11, an example of a demand prediction process of the present embodiment in the transport system 1 as described above will be described. FIG. 10 is a schematic diagram for explaining an example of a demand prediction process in the host management device 10 of FIG. 2, and FIG. 11 is a diagram illustrating an example of a demand prediction result output in the demand prediction process of FIG. 10.

In the transport system 1 according to the present embodiment, as described above, the electronic medical record information 420 is stored (registered) in the electronic medical record system 40, and information on some or all of the items of the electronic medical record information 420 can be transmitted to the host management device 10 or can be acquired from the host management device 10.

In addition, as described above, the transport system 1 according to the present embodiment stores (registers) management information including the lending schedule (including the use start time and the use end time), the use place, and the inventory status for each of the lending devices conveyed as the conveyed object by the mobile robot 20. This management information can be stored as part or all of the device lending information 324 and the temporary reservation information 325 in the storage unit 32 of the device lending system 30. Further, the management information can be stored as a part or all of the conveyed object information 126 in the storage unit 12 of the host management device 10.

As illustrated in FIG. 10, the demand prediction processing unit 110 inputs electronic medical record data such as the electronic medical record information 420 into the learned model 120 stored in the storage unit 12. Then, the demand prediction processing unit 110 acquires a demand prediction result that is a prediction result of the demand of the medical device after the lapse of the predetermined period (for example, the designated date and time) or at the time of the use start date and time from the learned model 120. FIG. 10 illustrates an example in which the predicted demand (A) at the time (t) is acquired as the demand prediction result.

Here, it is assumed that the input electronic medical record data describes information indicating the necessity of use of the medical device. The information includes information indicating a surgery necessary for the patient, information indicating a symptom of the patient, information indicating a treatment to the patient, information indicating the medical device itself, and the like, or information obtained by combining a plurality of pieces of the information. Therefore, in a case where information indicating the necessity of use of the medical device is described metaphorically or directly in the electronic medical record information 420 as illustrated in the procedure of FIG. 5, the input electronic medical record data corresponds to data of the electronic medical record information 420 itself or data including a description of the electronic medical record information 420.

However, the electronic medical record data input to the demand prediction processing unit 110 for prediction may be current electronic medical record data. That is, the electronic medical record data can be data excluding information about the medical device that has been returned after the lending of the electronic medical record information 420 has been completed.

The information predicted by the demand prediction processing unit 110 as the predicted demand (A) at the time (t) may include, for example, information indicating the predicted date and time of use and the number of used medical devices for each patient, as illustrated for a certain patient a in FIG. 11. Of course, the information predicted as the predicted demand (A) is not limited to the information indicating the patient ID, the patient name, the number of the patients, and the predicted use time for each medical device. In either case, the demand prediction result and the inventory prediction result described later can be obtained for each medical device. Further, the type of information predicted as the predicted demand (A) can be changed by changing the setting of an output parameter or the like at the time of generating the learned model 120 or by performing predetermined processing such as, for example, gathering data for each patient with respect to an output result from the learned model 120.

Figure 13:
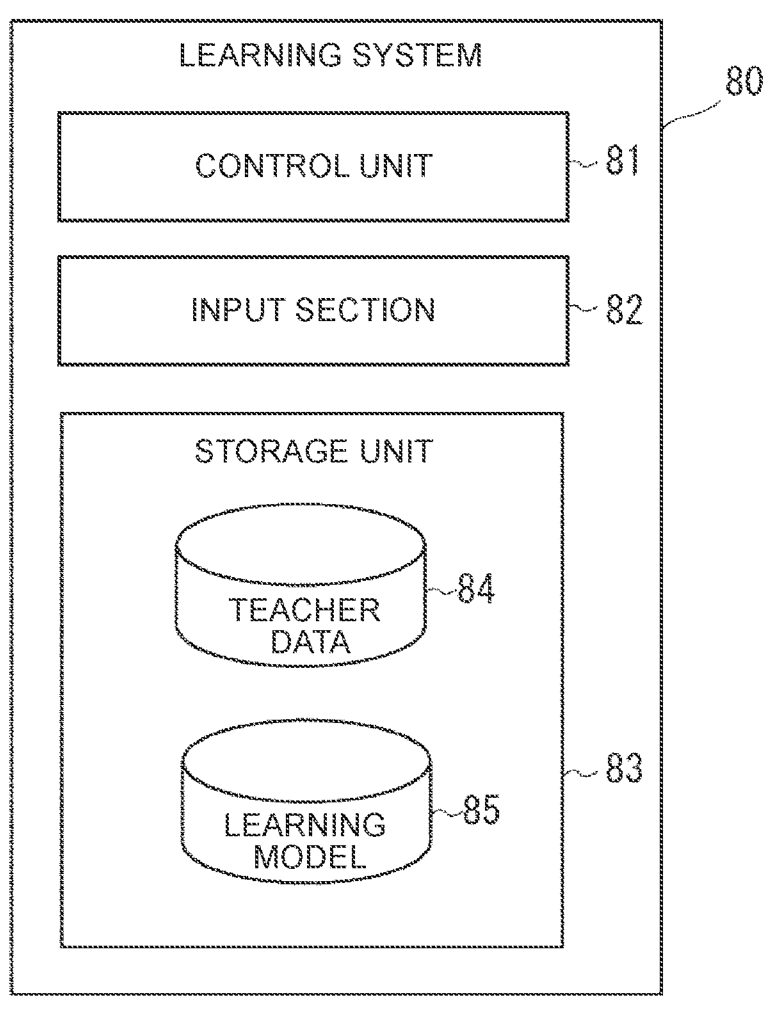
FIG. 13 is a block diagram illustrating a configuration example of a learning system that generates a learned model used in the host management device of FIG. 2.
Figure 14:
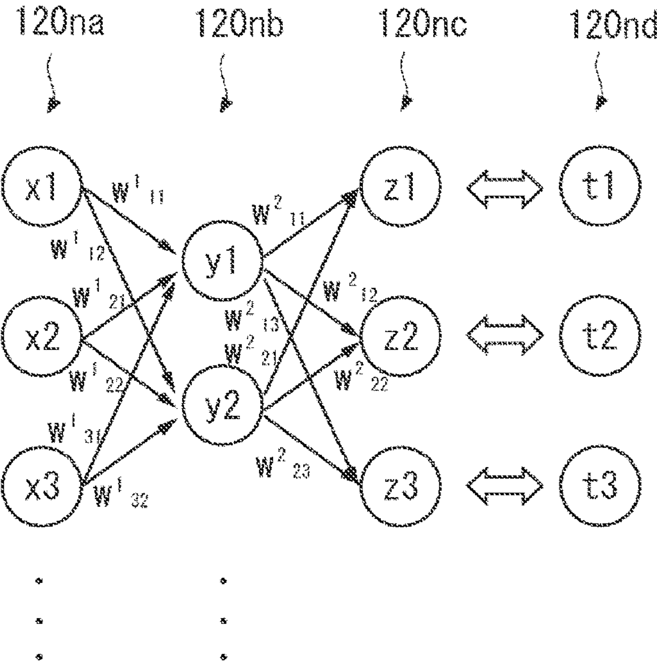
FIG. 14 is a schematic diagram illustrating an example of a learned model generated by the learning system of FIG. 13.

While FIGS. 13 and 14 are referred to below, as illustrated in FIG. 10, the learned model 120 is a model machine-learned by inputting learning data, which is historical data, into an unearned model 120*a*. Specifically, as described as processing in the demand prediction processing unit 110, the learned model 120 is a model in which machine learning is performed so as to output a demand prediction result by inputting electronic medical record data in which information indicating the necessity of use of the medical device is described using the above-described learning data. The learned model 120 may be updated by relearning at any time. Here, the above-described learning data is assumed to be teacher data including the loan result data and the electronic medical record data, as exemplified by the device lending information 324 and the electronic medical record information 420.

The lending result data included in the learning data may be data indicating a result of lending the medical device, and may include information about the medical device that has been conveyed in the device lending information 324, and may also include information about the medical device that is being conveyed. The loan result data may be, for example, data of some or all of the device lending information 324. However, since the loan result data is data including information indicating a loan result, it is preferable that the loan or the loan and the return of the device lending information 324 be the only data. For example, as the loan result data, among the device lending information 324 and the temporary reservation information 325 illustrated in FIG. 6, there may be no record corresponding to the temporary reservation information 325 (in this example, the record of the loan management number 003). There is no need for the type of maintenance personnel (or maintenance personnel). Further, the loan result data may not further include the scheduled user, and may not include the necessity of maintenance. However, by including the prospective user and necessity of maintenance, it is possible to make a prediction in consideration of the progress or delay of collection, etc. caused by the prospective user. In addition, it is possible to make predictions taking into account the time for which lending is impossible when maintenance is necessary. Note that the lending record data can also be obtained by separately accumulating the information on which lending or lending and return have been completed from the conveyed object information 126.

However, the loan result data may also include temporary reservation information 325. Specifically, as described above, the device lending system 30 may include a reservation system for provisionally reserving a lending of a medical device, and in such a configuration, the lending result data may include data in which information (temporary reservation information 325) indicating a medical device provisionally reserved by the reservation system and information (device lending information 324) indicating an actual lending result based on the provisional reservation are associated with each other. As a result, the learned model 120 can predict in advance the demand for the medical device in the device lending system 30 in response to the temporary reservation in the device lending system 30.

The electronic medical record data included in the learning data is the same item of information as the electronic medical record data input at the time of prediction, but is not the current electronic medical record data but is past electronic medical record data in which information indicating the necessity of use of the rented medical device is described. Again, the medical device lent out may include not only the medical device that has already been transported but also the medical device that is being transported.

Further, as illustrated in FIG. 10, the demand prediction processing unit 110 predicts the inventory of the medical device after the lapse of the predetermined time period or at the time of the start of use, based on the inventory information 323*a* indicating the present inventory and the temporary reservation information 325, and obtains the inventory prediction result that is the prediction result. The prediction process may be performed, for example, by the inventory prediction unit 110*b*, and the inventory prediction unit 110*b* may be provided, for example, in the demand prediction processing unit 110 or the device lending system 30. In addition, FIG. 10 illustrates an example in which the predicted inventory (B) at the time (t) is acquired as the inventory prediction result. As described above, the time point of the predetermined period or the use start date and time to be the prediction target of the inventory is the same as the time point of the predetermined period or the use start date and time at which the demand prediction is performed. Since the inventory prediction result is a result of estimating the inventory, it can also be referred to as an inventory estimation result.

Here, as described above, the inventory information 323*a* can be included in the device information 323 or the device lending information 324 as information indicating whether or not the device is lending. In addition to the temporary reservation information 325, the demand prediction processing unit 110 can also obtain an inventory prediction result based on the information of the device lending information 324 that has not yet been lent out of the medical devices, that is, the reservation information including the information about the medical devices before transportation and the inventory information 323*a*.

There is no particular method for predicting inventory. For example, the demand prediction processing unit 110 can perform prediction by simply subtracting the number of provisional reservations from, for example, the number of inventories at the time (t) (the number obtained by subtracting the number being lent or being lent and being transported from the number originally managed) for each medical device, and calculating the inventory. Alternatively, the demand prediction processing unit 110 may receive, from the device lending system 30, an inventory prediction result obtained by performing such calculation on the device lending system 30 side. Alternatively, the demand prediction processing unit 110 may acquire an inventory prediction result using a learned model for inventory prediction (not shown) for each medical device, or may receive, from the device lending system 30, an inventory prediction result obtained by performing such prediction on the device lending system 30 side, for example.

Then, the demand prediction processing unit 110 compares the predicted demand (A) acquired for the time (t) with the predicted inventory (B), when the demand at the time (t) exceeds the inventory, that is, when A>B, it is determined that there is a possibility that a specific medical device is out of stock, and notifies the device lending system 30 via the communication unit 14. This notification can be executed via the communication unit 14 by the notification processing unit 110*c* included in the demand prediction processing unit 110. The notification content may include that the demand has exceeded the inventory, the medical device of the subject, the date and time of the exceedance, and the like.

Upon receiving the notification, the device lending system 30 notifies at least one of the administrator and the lending staff. The notification destination may be registered in advance as an e-mail address, a number of a short message, or the like in the storage unit 32. Incidentally, a device lending system can be constructed including these notification destinations, and in this case, these notification destinations become notification destinations by the demand prediction processing unit 110.

With such a configuration, the host management device 10 can predict in advance the demand for the medical device in the device lending system 30. The reason is as follows: That is, since the use of the medical device is determined according to the symptom and the treatment of the patient, it is possible to predict which medical device is likely to be used based on the information on the treatment and the surgery recorded in the electronic medical record information 420 and the information on the nursing and the progress. Further, since the actual use includes a case determined by the judgment of the doctor or the nurse, the demand cannot be accurately predicted only by the information input to the electronic medical record information 420 before the use of the medical device. However, the host management device 10 can predict the demand based on the past lending record in addition to the electronic medical record information 420. Further, in order to improve the prediction accuracy as needed, the accumulated data may be relearned and the learned model 120 may be updated.

Then, the host management device 10 refers to, for example, the electronic medical record information 420, and predicts the demand of the medical device as described above and notifies each patient who is being hospitalized and is scheduled to be hospitalized, other treatment, and other treatment schedules as necessary. In fact, when the demand is rapidly increased when the demand for lending of the medical device cannot be predicted in advance, the inventory shortage occurs, in the host management device 10 according to the present embodiment, since it is possible to predict the lending demand, it is possible to take measures toward securing the inventory before the inventory shortage.

Figure 12:
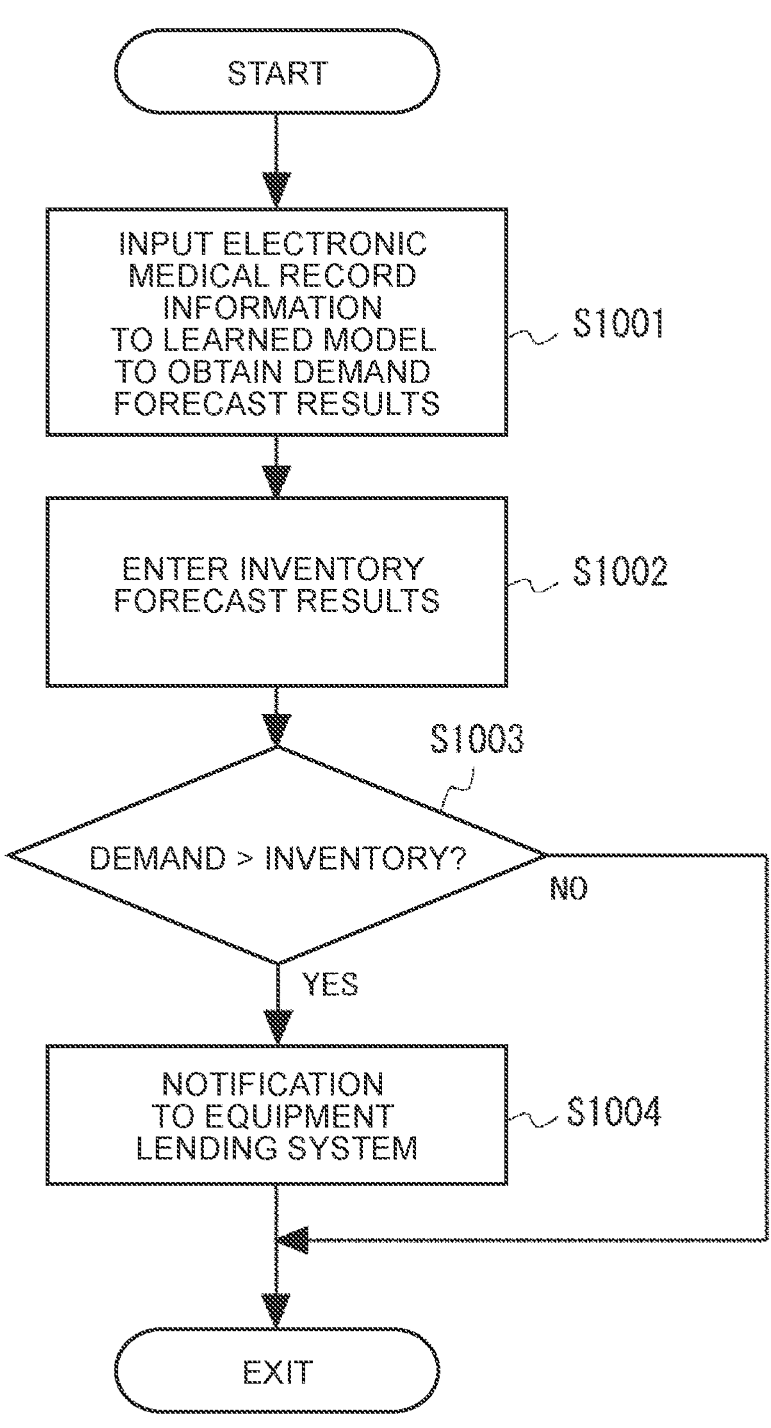
FIG. 12 is a flowchart illustrating a demand prediction method according to the present embodiment.

Next, an example of a flow of the demand prediction method according to the present embodiment will be briefly described with reference to FIG. 12. FIG. 12 is a flowchart illustrating a demand prediction method according to the present embodiment.

First, the host management device 10 acquires the electronic medical record information 420 by receiving it from the electronic medical record system 40. The host management device 10 inputs the information to the learned model 120 and acquires a demand forecast (S1001). Next, the host management device 10 receives the information from the device lending system 30 and inputs the inventory estimation result (S1002). The order of S1001, S1002 of steps is not limited. Further, it is assumed that the electronic medical record information 420 and the inventory prediction result input in both steps include those of the same date and time as each other and include those of the same medical device.

Next, the host management device 10 determines whether or not the demand indicated by the demand prediction result is larger than the stock indicated by the inventory prediction result (S1003). When the demand indicated by the demand prediction result is larger than the inventory indicated by the inventory prediction result (YES by S1003), the host management device 10 notifies the device lending system 30 (S1004), and ends the process. On the other hand, if S1003 of steps is NO, the host management device 10 ends the process as it is. Such a process can be executed for each medical device to be lent.

Learning System

Referring to FIGS. 13 and 14, a configuration example of a learning system that generates the above-described learned model and a processing example (an example of a learning method) in the learning system will be described. FIG. 13 is a block diagram illustrating a configuration example of a learning system that generates a learned model used in the host management device 10 of FIG. 2. FIG. 14 is a schematic diagram illustrating an example of a learned model generated by the learning system 80 of FIG. 13. Note that the non-learning model is the same as the configuration shown in FIG. 14, but is a model in which the weight coefficient is not determined.

The learning system 80 illustrated in FIG. 13 may include a control unit 81, an input unit 82, and a storage unit 83. The learning system 80 may be constructed using a computer such as a PC for learning (e.g., Artificial Intelligence (AI)). However, the learning system 80 may be configured by a single device or may be configured by distributing functions among a plurality of devices.

The control unit 81 controls the entire learning system 80. The control unit 81 can be realized by, for example, an integrated circuit. The control unit 81 can be realized by, for example, a processor, a working memory, a nonvolatile storage device, and the like. The control program executed by the processor is stored in the storage device, and the processor reads the program into the working memory and executes the program, whereby the function of the control unit 81 can be performed. The control program includes a learning program for executing learning. Note that the storage unit 83 can also be used as the storage device.

The input unit 82 can be constituted by at least one of an interface that performs an input operation of data, and a communication interface that inputs data from an external device by communication. The input unit 82 inputs a data set of learning data (teacher data) 84 necessary for learning, and stores the data set in the storage unit 83 so as to be referred to at the time of learning. The storage unit 83 may store the teacher data 84, and may store a learning model 85 as an untrained model.

In the processing by the learning system 80, the control unit 81 may input the teacher data 84 to the learning model 85 as the non-learning model, execute the machine learning based on the teacher data 84, and set the learning model 85 as the learned model 120. As described above, the learned model 120 is generated as a model subjected to machine learning so as to input electronic medical record data in which information indicating the necessity of use of the medical device is described and output a demand prediction result. With such a configuration, the learned model 120 can predict in advance the demand for the medical device in the device lending system 30.

For example, a neural network 120*n* as illustrated in FIG. 14 may be used as the learning model 85. The neural network 120*n* of FIG. 14 may include an input layer 120*na*, a hidden layer (intermediate layer) 120*nb*, and an output layer 120*nc*, and may include a value corresponding to the output layer 120*nc* as a correct data 120*nd*. For simplicity of explanation, the intermediate layer 120*nb* is described as one layer, but the intermediate layer 120*nb* may be two or more layers.

The input layer 120*na* includes an input node that uses each of the explanatory variables x1, x2, x3, . . . as an input parameter. In the node indicated by the value y1 among the intermediate layer 120*nb*, a value obtained by multiplying the input parameter x1 by the weighting coefficient $w^1{}_{11}$, a value obtained by multiplying the input parameter x2 by the weighting coefficient $w^1{}_{21}$, a value obtained by multiplying the input parameter x3 by the weighting coefficient $w^1{}_{31}$, and the like are input, and the sum of the values is calculated. In the node indicated by the value y2 among the intermediate layer 120*nb*, a value obtained by multiplying the input parameter x1 by the weighting coefficient $w^1{}_{12}$, a value obtained by multiplying the input parameter x2 by the weighting coefficient $w_1{}^{22}$, a value obtained by multiplying the input parameter x3 by the weighting coefficient $w_1{}^{32}$, and the like are input, and the sum of the values is calculated. The same applies to other nodes of the intermediate layer 120*nb*.

The output layer 120*nc* includes an output node that uses each of the objective variable z1, z2, z3, . . . as an output parameter. In the output node indicated by the value z1 of the output layer 120*nc*, a value obtained by multiplying the value y1 by the weighting factor $w^2{}_{11}$, a value obtained by multiplying the value y2 by the weighting factor $w^2{}_{21}$, and the like are inputted, and the sum thereof is calculated and compared with the value t1 of the corresponding correct data 120*nd*. In the output node indicated by the value z2 of the output layer 120*nc*, a value obtained by multiplying the value y1 by the weighting factor $w^2{}_{12}$, a value obtained by multiplying the value y2 by the weighting factor $w^2{}_{22}$, and the like are inputted, and the sum thereof is calculated and compared with the value t2 of the corresponding correct data 120*nd*. The same applies to other output nodes of the output layer 120*nc*.

In accordance with such comparison, the respective weighting factors are calculated so that the comparison result is small, so that the non-learned neural network 120*n* is generated as the learned model 120. That is, when the actual result is given as the correct data 120*nd*, the control unit 81 adjusts the respective weighting factors so as to minimize the respective errors with respect to the value of the output-node 120*nc* of the output-layer z1, z2, z3, . . . and the value t1, t2, t3, . . . of the corresponding correct data 120*nd*, and thereby generates the learned model 120. Here, minimizing each error may refer to minimizing, for example, the sum of each error or the sum of squares of each error.

The teacher data 84 used in generating the learned model 120 may be a data set including electronic medical record data and loan result data as described above. Information of each item included in the electronic medical record data is input as an input parameter x1, x2, x3, . . . , and information of each item included in the loan result data can be set as a value t1, t2, t3, . . . of the correct data 120*nd*. When the output illustrated in FIG. 11 is performed, the value of the correct data 120*nd* may include, for example, information indicating the medical device (for example, information indicating the type of the medical device), the number of the medical devices, and a value indicating the time and date or time period to be used. At the time of prediction (at the time of operation), the value of the node corresponding to each of the output-layer 120*c* indicates the demand prediction result. Also, as discussed above, the input parameters may include information directly indicative of the medical device. However, even if the information directly indicating the medical device is not included, it is sufficient that the information metaphorically indicating the medical device, such as a symptom and a treatment, is included.

Although the electronic medical record data has been described as a simple example in FIG. 5, the electronic medical record data may include the following items in more detail. For example, the electronic medical record may include, but may not include, the patient ID and/or name, age, gender, etc., identifying the patient, for example, as the patient information. In addition, the electronic medical record data may include, as information related to the hospitalization among the information related to the treatment, a hospitalization date and time, a medical department at the time of hospitalization, an inpatient ward, an attending physician, a nurse in charge, a disease name, a hospitalization purpose, an examination date, an examination name, an operation name, an operation date, and the like. The electronic medical record data may include, for example, at least one of Activities of Daily Living (ADL), a nursing plan, and a nursing progress chart, and at least one of a clinical pass and a pass status. Further, the electronic medical record data may include information directly indicating the use of the medical device as described above, and may include information indicating how many days after processing such as surgery, information indicating the severity, information indicating the judgment of a doctor, and the like. However, the electronic medical record data is not limited to including all of the above-described items, and may include only a part thereof, and may further include additional items. In particular, in order to suppress a decrease in prediction accuracy due to pseudo-correlation or the like, items of information to be included as electronic medical record data can be added/deleted as appropriate according to a judgment of a person who performs model construction or the like.

As illustrated in FIG. 11, the loan record data may include items of information such as the type of medical device that may be used, the number of units required, and the estimated use time, but the present disclosure is not limited thereto.

The learned model 120 thus generated is updated by updating the results and setting the updated results as correct data 120*nd* so that the respective weighting factors are adjusted so as to minimize an error between the output node of the output layer 120*nc* and the corresponding results. That is, the learning model 85 as the learned model 120 can be relearned based on a newly prepared data set when relearning is required.

Further, the electronic medical record data to be included in the learning data and the electronic medical record data to be input at the time of predicting the demand may include information indicating that the medical staff has determined the use of the medical device. Thus, the demand prediction processing unit 110 can more accurately predict the demand of the medical device in advance in consideration of the result of the medical staff determining the use of the medical device.

In addition, the lending record data may include information indicating an end time or a return time of use of the medical device. This information in the loan result data corresponds to information indicating the end time of the treatment in the electronic medical record data. Therefore, the demand prediction processing unit 110 can more accurately predict the demand of the medical device in advance in consideration of the end time or the return time of the actual use of the medical device.

Note that the inventory prediction illustrated in the inventory prediction unit 110*b* of FIG. 10 can also be executed using the learned model, and the learning process in that case also differs only in the algorithm, the teacher data, and the like, so that the same learning system can be used. In this case, by executing the machine learning by inputting the past inventory prediction data and data indicating the inventory performance at the date and time actually corresponding to the learning data to the non-learning model as learning data, the current inventory prediction data is input to generate a learned model such that the inventory prediction result is output.

Other

Part or all of the processing in the prediction system, the host management device 10, the mobile robot 20, the device lending system 30, the electronic medical record system 40, the learning system 80, and the like described above can be realized as a computer program. Such programs include instructions (or software code) that, when loaded into a computer, cause the computer to perform one or more of the functions described in the embodiments. The program may be stored in a non-transitory computer-readable medium or a tangible storage medium. By way of example, and not limitation, computer-readable media or tangible storage media include random-access memory (RAM), read-only memory (ROM), flash memory, solid-state drive (SSD) or other memory techniques, CD-ROM, digital versatile disk (DVD), Blu-ray disk or other optical disk storage, magnetic cassettes, magnetic tape, magnetic disk storage or other magnetic storage devices. The program may be transmitted on a transitory computer-readable medium or a communication medium. The example of the transitory computer-readable medium or the communication medium includes, but is not limited to, an electrical, optical, acoustic, or other form of propagating signal.

The present disclosure is not limited to the above-described embodiments, and can be appropriately modified without departing from the scope of the present disclosure. Further, the present disclosure includes that each example in the above-described embodiment is appropriately combined and implemented.

For example, although the above-described embodiment mainly describes a system in which a mobile robot autonomously moves in a hospital, the above-described transport system is not limited to a medical device, and can transport an article including a device to be lent as a package in a hotel, a restaurant, an office building, an event hall, or a complex facility. That is, the prediction system according to the above-described embodiment can be used to predict demand for a lending device other than a medical device. In addition, although the description has been given on the assumption that the device is transported in one facility, the present disclosure can be similarly applied to transportation between a plurality of facilities as long as the mobile robot is a mobile robot that can be transported between a plurality of facilities. In addition, the above-described transport system is not limited to the case of using the mobile robot 20 described as an example, and a mobile robot having various configurations may be used instead of or in addition to the mobile robot.

The prediction system according to the present embodiment can also be applied to a case where a medical device to be lent is transported without using a mobile robot or a case where another type of device to be lent is transported without using a mobile robot.

What is claimed is:

1. A prediction and conveyance system for predicting a demand for a medical device in a medical device lending system, the prediction and conveyance system comprising, a host management device, and a mobile robot comprising a sensor configured to detect external obstacles, the mobile robot being configured to:

autonomously travel to transport the medical device within a medical facility, and convey the medical device to a destination in the medical facility included in a conveyance request, and decelerate or stop when executing the conveyance request, based on output from the sensor indicating that a distance from a peripheral object to the mobile robot becomes equal to or less than a distance threshold value, wherein the host management device includes a storage unit, an arithmetic unit configured to receive the conveyance request for the medical device from a user, and a communication unit, and the storage unit:

stores a trained model that has undergone machine learning to output a demand prediction result that is a prediction result of the demand for the medical device by inputting electronic chart data describing information showing a necessity of use of the medical device, using training data including lending record data indicating a record of the medical device that has been lent and the electronic chart data describing information indicating the necessity of the use of the medical device that has been lent;

the arithmetic unit includes a demand prediction unit, and the demand prediction unit:

inputs the electronic chart data describing the information indicating the necessity of the use of the medical device into the trained model to acquire the demand prediction result; and inputs an inventory prediction result that is a prediction result of an inventory of the medical device, the prediction result being predicted based on a present inventory and reservation information; and compares the acquired demand prediction result with the input inventory prediction result, and the communication unit: sends a notification to the medical device lending system when the demand exceeds the inventory, and the arithmetic unit:

generates route planning information for the mobile robot based on the conveyance quest, and instructs the mobile robot so as to cause the mobile robot to travel to the destination in the medical facility included in the conveyance request based on the generated route planning information.

2. The prediction and conveyance system according to claim 1, wherein:

the medical device lending system includes a reservation system for temporarily reserving lending of the medical device; and the lending record data includes data in which information indicating the medical device temporarily reserved by the reservation system is associated with information indicating a record of actual lending based on a temporary reservation.

3. The prediction and conveyance system according to claim 1, wherein the electronic chart data includes information indicating that medical staff has determined the use of the medical device.

4. The prediction and conveyance system according to claim 1, wherein the lending record data includes information indicating an end time or a return time of the use of the medical device.

5. The prediction and conveyance system according to claim 1, wherein the communication unit notifies a necessity of maintenance to a maintenance person when maintenance of consumables is necessary.

6. The prediction and conveyance system according to claim 1, wherein the host management device generates the route planning information by setting passing points from a starting point and the destination included in the conveyance request, so as to avoid locations with a predetermined degree of congestion.

7. A prediction and conveyance method for predicting, by a computer, a demand for a medical device in a medical device lending system and controlling a mobile robot, the prediction and conveyance method comprising:

storing, by the computer, a trained model that has undergone machine learning to output a demand prediction result that is a prediction result of the demand for the medical device by inputting electronic chart data describing information showing a necessity of use of the medical device, using training data including lending record data indicating a record of the medical device that has been lent and the electronic chart data describing information indicating the necessity of the use of the medical device that has been lent;

inputting, by the computer, the electronic chart data describing the information indicating the necessity of the use of the medical device into the learned trained model to acquire the demand prediction result;

inputting, by the computer, an inventory prediction result that is a prediction result of an inventory of the medical device, the prediction result being predicted based on a present inventory and reservation information;

comparing, by the computer, the acquired demand prediction result with the input inventory prediction result, and notifying the medical device lending system when the demand exceeds the inventory;

receiving, by the computer, a conveyance request for the medical device from a user;

generating, by the computer, route planning information for the mobile robot based on the conveyance request, and instructing the mobile robot so as to cause the mobile robot to travel to a destination in a medical facility included in the conveyance request, based on the generated route planning information, and controlling the mobile robot the mobile robot comprising a sensor configured to detect external obstacles, to:

autonomously travel to transport the medical device within the medical facility, convey the medical device to the destination in the medical facility included in the conveyance request and decelerate or stop when executing the conveyance request, based on output from the sensor indicating that a distance from a peripheral object to the mobile robot becomes equal to or less than a distance threshold value.

8. The prediction and conveyance method according to claim 7, wherein:

the medical device lending system includes a reservation system for temporarily reserving lending of the medical device; and the lending record data includes data in which information indicating the medical device temporarily reserved by the reservation system is associated with information indicating a record of actual lending based on a temporary reservation.

9. The prediction and conveyance method according to claim 7, wherein the electronic chart data includes information indicating that medical staff has determined the use of the medical device.

10. The prediction and conveyance method according to claim 7, wherein the lending record data includes information indicating an end time or a return time of the use of the medical device.

* * * * *